(12) United States Patent
Andersen

(10) Patent No.: US 12,187,782 B2
(45) Date of Patent: *Jan. 7, 2025

(54) PDL1 PEPTIDES FOR USE IN CANCER VACCINES

(71) Applicant: IO BIOTECH APS, Copenhagen (DK)

(72) Inventor: Mads Hald Andersen, Naerum (DK)

(73) Assignee: IO Biotech ApS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,277

(22) Filed: May 27, 2022

(65) Prior Publication Data
US 2022/0372108 A1 Nov. 24, 2022

Related U.S. Application Data

(63) Continuation of application No. 16/310,908, filed as application No. PCT/EP2017/065122 on Jun. 20, 2017, now abandoned.

(30) Foreign Application Priority Data

Jun. 21, 2016 (EP) ..................... 16175397

(51) Int. Cl.
| | |
|---|---|
| A61K 38/00 | (2006.01) |
| A61K 39/395 | (2006.01) |
| A61K 45/06 | (2006.01) |
| A61P 35/00 | (2006.01) |
| C07K 14/705 | (2006.01) |
| A61K 39/00 | (2006.01) |

(52) U.S. Cl.
CPC .... *C07K 14/70596* (2013.01); *A61K 39/3955* (2013.01); *A61K 45/06* (2013.01); *A61P 35/00* (2018.01); *A61K 2039/545* (2013.01); *A61K 2039/55511* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 9,669,078 B2 * | 6/2017 | Andersen | A61P 37/06 |
| 2003/0044768 A1 | 3/2003 | Wood et al. | |
| 2009/0297518 A1 | 12/2009 | Honjo et al. | |
| 2011/0081341 A1 | 4/2011 | Honjo et al. | |
| 2011/0195068 A1 | 8/2011 | Langermann et al. | |
| 2014/0242101 A1 * | 8/2014 | Andersen | A61P 43/00 424/185.1 |
| 2020/0299401 A1 * | 9/2020 | Andersen | C07K 16/2896 |
| 2020/0339659 A1 | 10/2020 | Andersen | |

FOREIGN PATENT DOCUMENTS

| | | | | |
|---|---|---|---|---|
| WO | WO-8807547 A | * | 10/1988 | C07K 14/61 |
| WO | WO-01034768 A2 | | 5/2001 | |
| WO | WO-2002086083 A2 | | 4/2002 | |
| WO | WO-2008085562 A2 | | 7/2008 | |
| WO | WO-2009026472 A1 | | 2/2009 | |
| WO | WO-2010027828 A2 | | 3/2010 | |
| WO | WO-2011066342 A2 | | 6/2011 | |
| WO | WO-2011109789 A2 | | 9/2011 | |
| WO | WO-2013056716 A1 | | 4/2013 | |

OTHER PUBLICATIONS

Pepscan.com accessed on Apr. 13, 2023 at www.pepscan.com/custom-peptide-synthesis/peptide-modifications/c-terminal-modifications/ (Year: 2015).*
Ahmad SM, et al., "Harnessing PD-L1-specific cytotoxic T cells for anti-leukemia immunotherapy to defeat mechanisms of immune escape mediated by the PD-1 pathway," Leukemia, vol. 28:236-238 (2014).
Andersen, M. et al., "Identification of a Cytotoxic T Lymphocyte Response to the Apoptosis Inhibitor Protein Surviving in Cancer Patients," Cancer Res, vol. 61: 869-872 (2001).
Andersen MH, et al., "Identification of heme oxygenase-1-specific regulatory CD8+ T cells in cancer patients," J Clin Invest., vol. 119:2245-2256 (2009).
Andersen MH., "Immune Regulation by Self-Recognition: Novel Possibilities for Anticancer Immunotherapy," J Natl Cancer Inst., vol. 107:154: 8 pages. (2015).
Andersen, MH., "The targeting of immunosuppressive mechanisms in hematological malignancies," Leukemia, vol. 28:1784-1792 (2014).
Benavides, L. et al., "Comparison of different HER2/neu vaccines in adjuvant breast cancer trials: implications for dosing of peptide vaccines," Expert Review of Vaccines, vol. 10(2): 201-210 (2011).
Berntsen A., et al., "Therapeutic dendritic cell vaccination of patients with metastatic renal cell carcinoma: a clinical phase 1/2 trial," J Immunother. vol. 31:771-780 (2008).
Bijker, et al., "CD8+ Ctl Priming by Exact Peptide Epitopes in Incomplete Freund's Adjuvant Induces a Vanishing CTL Response, whereas Long Peptides Induce Sustained CTL Reactivity," J Immunol., vol. 179:5033-5040 (2007).
Borch, TH, et al., "Reorienting the immune system in the treatment of cancer by using anti-PD-1 and anti-PD-L1 Antibodies," Drug Discov Today, vol. 20:1127-1134 (2015).
Brahmer, JR, et al., "Safety and Activity of Anti-PD-10 L1 Antibody in Patients with Advanced Cancer," N Engl J Med., vol. 366:2455-2465 (2012).
Chen, Z, et al., "Th17 cells: a new fate for differentiating helper T cells," Immunol Res vol. 41:87-102. (2008).
Colman, P. et al., "Effects of amino acid sequence changes on antibody-antigen interactions," Research in Immunology, vol. 145(1): 33-36 (1994).

(Continued)

*Primary Examiner* — Aradhana Sasan
*Assistant Examiner* — Mercy H Sabila
(74) *Attorney, Agent, or Firm* — COOLEY LLP

(57) ABSTRACT

The present invention relates to a PD-L1 peptide fragment, useful in cancer therapies as well as PD-L1 peptide fragments for use in a method for treatment or prevention of a cancer, when administered simultaneously or sequentially with an additional cancer therapy.

5 Claims, 16 Drawing Sheets
Specification includes a Sequence Listing.

(56) References Cited

OTHER PUBLICATIONS

Dong H, et al., "B7-H1, a third member of the B7 family, costimulates T-cell proliferation and interleukin-10 secretion," Nat Med., vol. 5:1365-1369 (1999).
Francisco, L. et al., "The PD-1 pathway in tolerance and autoimmunity," Immunological Reviews, vol. 136(1): 219-242 (2010).
Hamanishi, J. et al., "Programmed cell death 1 ligand 1 and tumor-infiltrating CD8(+) T lymphocytes are prognostic actors of human ovarian cancer," Proceedings of the National Academy of Sciences, vol. 104(9): 3360-3365 (2007).
Hansen M. et al., "Cellular based cancer vaccines: type 1 polarization of dendritic cells," Curr Med Chem., vol. 19:4239-4246 (2012).
Hino, R. et al., "Tumor Cell Expression of Programmed Cell Death-1 Ligand 1 is a prognostic factor for malignant melanoma," Cancer, vol. 116(7): 1757-1766 (2010).
Jeffery H. et al., "The Preparation and Characterization of Poly(lactide-co-glycolide) microparticles. II. The entrapment of a model protein using a (water-in-oil)-in water emulsion solvent evaporation technique," Pharm. Res., vol. 10:362-368 (1993).
Jurado, J et al., "Programmed death (PD)-1: PD-ligand 2 pathway inhibits T cell effector functions during human tuberculosis," Journal of Immun., vol. 181(1): 116-125 (2008).
Kozako, T, et al., "PD-1/PD-L1 expression in human T-cell leukemia virus type 1 carriers and adult T-cell leukemia/lymphoma patients," Leukemia, vol. 23:375-382 (2009).
Lederman, S. et al., "A single amino acid substitution in a common African allele of the CD4 molecule ablates binding of the monoclonal antibody, OKT4," Molecular Immunology, vol. 28(11): 1171-1181 (1991).
Metzler, W. et al., "Solution structure of human CTLA-4 and delineation of a CD80/CD86 binding site conserved in CD28," Nature Structural Biol., vol. 4(7):527-531 (1997).
Munir, S, et al., "Cutaneous T cell lymphoma cells are targets for immune checkpoint ligand PD-L1-specific, cytotoxic T cells," Leukemia, vol. 27:2251-2253 (2013).
Munir, S, et al., "HLA-restricted cytotoxic T cells that are specific for the immune checkpoint ligand PD-L1 occur with high frequency in cancer patients," Cancer Research, vol. 73:1674-1776 (2013).
Munir, S, et al., "The immune checkpoint regulator PD-L1 is a specific target for naturally occurring CD4+ T cells," Oncoimmunology, vol. 2:e23991 (2013).
Nomi, T. et al., "Clinical significance and therapeutic potential of the programmed death-1 ligand/programmed death-1 pathway in human pancreatic cancer," Clinical Cancer Research, vol. 13(7): 2151-2157 (2007).
Pardoll, DM, "The blockade of immune checkpoints in cancer immunotherapy," Nat Rev Cancer, vol. 12:252-264 (2012).
Rammensee, HG, et al., "MHC molecules as peptide receptors," Curr Biol., vol. 5:35-44 (1993).
Rentero, I. et al., "Screening of large molecule diversities by phage display," Chimia, vol. 65(11): 843-845 (2011).
Seo, SK, et al., "Attenuation of IFNgamma-induced B7-H1 expression by 15-deoxy-delta(12,14)-prostaglandin J2 via downregulation of the Jak/STAT/IRF-1 signaling 45 pathway," Life Sci., vol. 112:82-89 (2014).
Sharpe, A. et al., "The function of programmed cell death 1 and its ligands in regulating autoimmunity and infection," Nature Immunology, vol. 8(3): 239-245 (2007).
Stanciu, L. et al., "Expression of programmed death-1 ligand (PD-L) 1, PD-L2, B7-H3, and inducible costimulator ligand on human respiratory tract epithelial cells and regulation by respiratory syncytial virus and type 1 and 2 cytokines," Journal of Infectious Diseases, vol. 193(3): 404-412 (2006).
Tamura, H. et al., "B7-H1 costimulation preferentially enhances CD28-independent T-helper cell function," Blood 97(6):1809-1816 (2001).
Tewalt. EF, et al., "Lymphatic endothelial cells induce tolerance via PD-L1 and lack of co-stimulation leading to high-level PD-1 expression on CD8 T cells," Blood, vol. 120:4772-4782. (2012).
Thompson, R. et al., "Costimulatory B7-H1 in renal cell carcinoma patients: Indicator of tumor aggressiveness and potential therapeutic target," Proceedings of the National Academy of Sciences, vol. 101(49): 17174-17179 (2004).
Topalian, SL, et al., "Safety, Activity, and Immune Correlates of Anti-PD-1 Antibody in Cancer," N Engl J Med., vol. 366:2443-2453 (2012).
Yang, XO, et al., "Molecular antagonism and plasticity of regulatory and inflammatory T cell programs," Immunity, vol. 29:44-56 (2008).
Zou, W, et al., "T(H)17 cells in tumour immunity and immunotherapy," Nat Rev Immunol vol. 10:248-256 (2010).

* cited by examiner

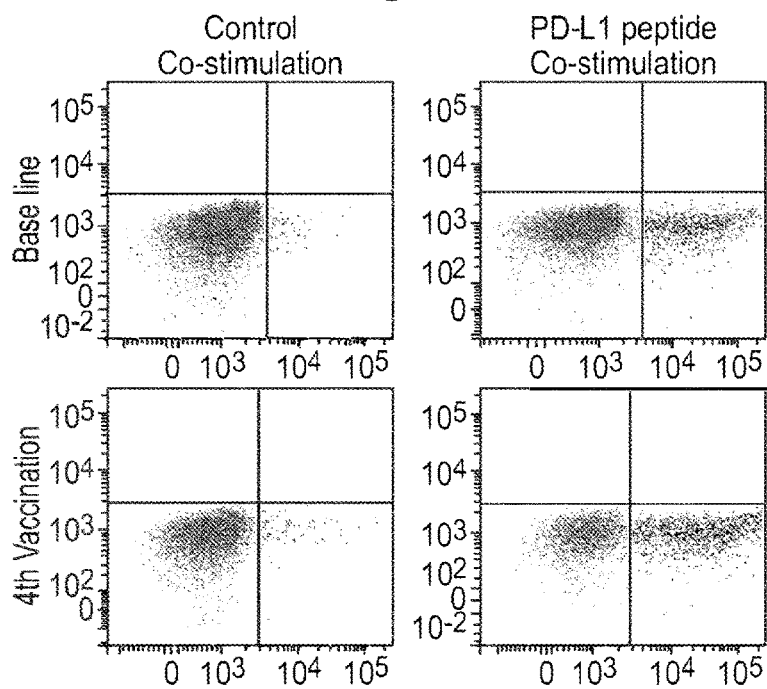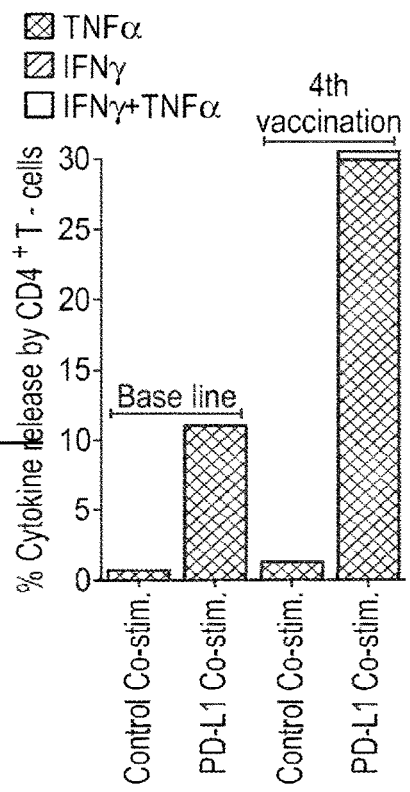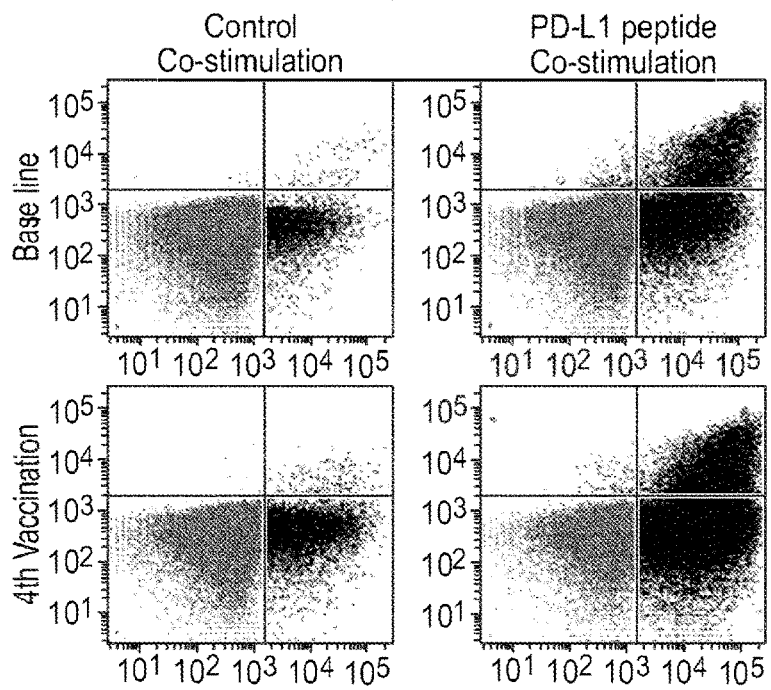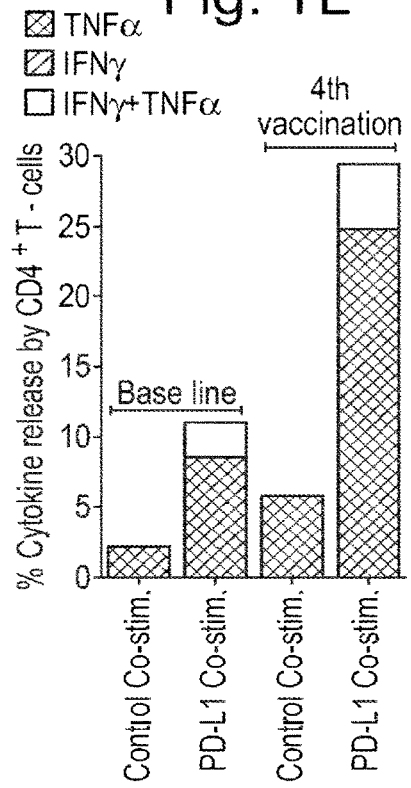

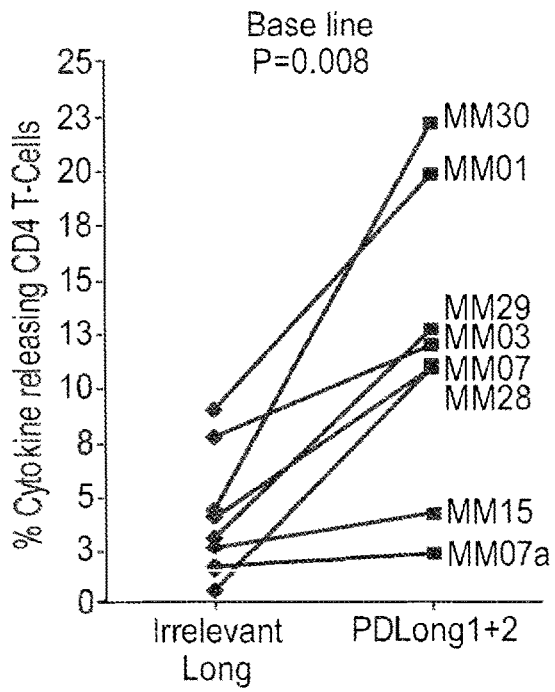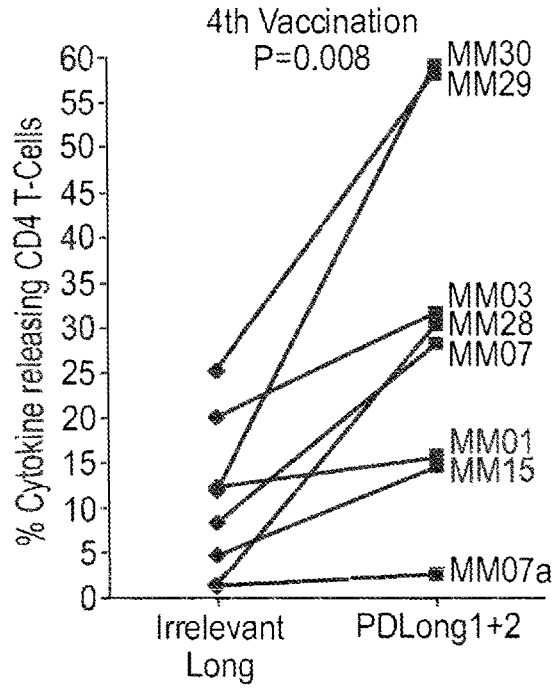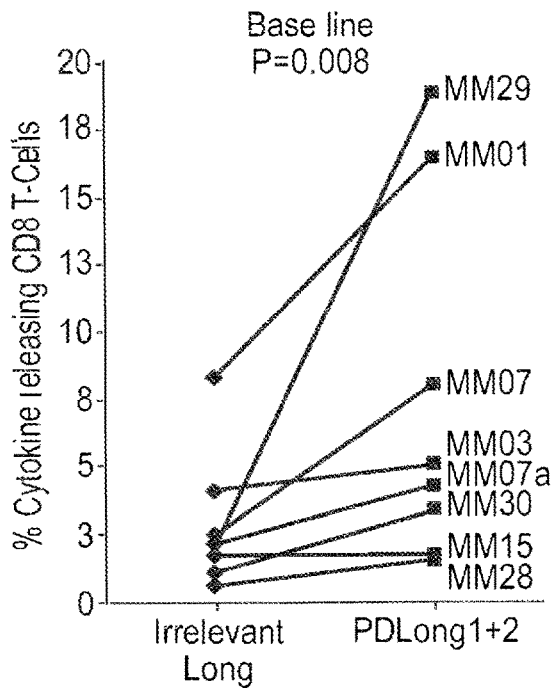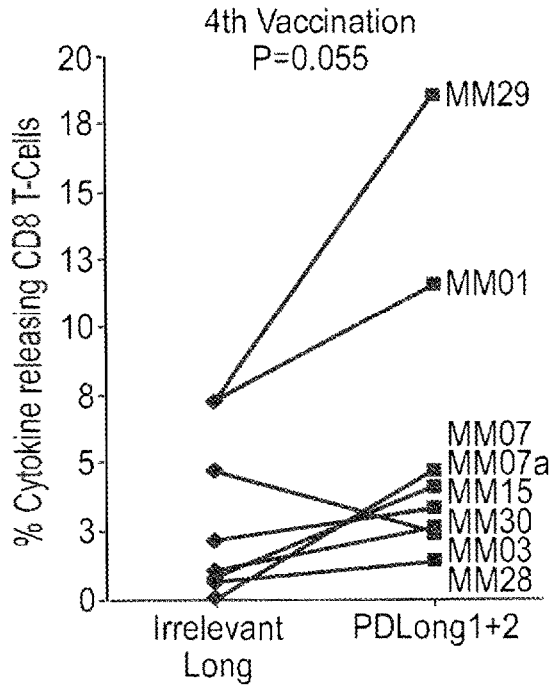

PDL1 PEPTIDES FOR USE IN CANCER VACCINES

CROSS-REFERENCE TO RELATED APPLICATIONS

This application is a continuation of U.S. Utility application Ser. No. 16/310,908, filed Dec. 18, 2018, which is now abandoned, which is a § 371 National Stage Entry of International Application PCT/EP2017/065122, filed Jun. 20, 2017, which claims priority to EP Application No. 16175397.5, filed Jun. 21, 2016, the contents of each of which are herein incorporated by reference in their entireties.

DESCRIPTION OF THE TEXT FILE SUBMITTED ELECTRONICALLY

The present application is being filed along with a sequence listing in electronic format. The sequence listing is provided as a file entitled, "IOBT-010/02US Sequence Listing.txt", created on May 26, 2022 which is 32.0 Kb in size. The information in the electronic format of the sequence listing is incorporated herein by reference in its entirety.

TECHNICAL FIELD

The present invention relates to novel PD-L1 peptide fragments, as well as compositions, uses, and kit-of-parts comprising these peptide fragments. Furthermore, the invention concerns PD-L1 peptide fragments for use in a method for treatment or prevention of a cancer, when administered simultaneously or sequentially with an additional cancer therapy.

BACKGROUND ART

The immune system has the capacity to recognize and destroy neoplastic cells; nevertheless, despite the fact that neoplastic transformation is associated with the expression of immunogenic antigens, the immune system often fails to respond effectively to these antigens. The immune system becomes tolerant towards these antigens. When this happens, the neoplastic cells proliferate uncontrollably leading to the formation of malignant cancers with poor prognosis for the affected individuals. The acquired state of tolerance must be overcome for cancer immunotherapy to succeed. Several lines of evidence suggest that T cells are the main effectors in the immunological response against cancer cell. Immune regulatory proteins like indoleamine 2,3-dioxygenase (IDO), Cytotoxic T lymphocyte antigen 4 (CTLA-4) and Programmed cell death 1 ligand 1 (PD-L1) play a vital role in the immune suppression and tolerance induction of anti-cancer immune responses. CTLA-4 is a key negative regulator of T-cell responses, which can restrict the antitumor immune response.

Recently, the anti-CTLA-4 antibody ipilimumab was approved by the FDA as well as EMEA for the treatment of melanoma after showing effect in clinical phase III studies.

Another central mechanism counteracting tumor-specific immunity and preventing effective anticancer immunotherapy requires a specific environment in which tolerogenic dendritic cells (DC) play an essential role deviating the immune response away from effective immunity.

Programmed death-1 (PD1) is a regulatory surface molecule delivering inhibitory signals important to maintain T-cell functional silence against their cognate antigens. Its ligands, known as PD-L1 and PD-L2, or B7-H1 and B7-H2 are expressed on APCs, tumor cells, placental, and nonhematopoietic cells found in an inflammatory microenvironment. Interference with PD-1 or its ligand PD-L1 increases antitumor immunity. It appears that upregulation of PD-L1 is a mechanism that cancers can employ to evade the host immune system. Expression of PD-L1 on tumors correlates with poor clinical outcome for a number of cancers including pancreas, renal cell, ovarian, head and neck, and melanoma (Hamanishi et al., 2007, *Proc. Natl. Acad. Sci. U.S.A* 104:3360-3365; Nomi et al., 2007, *Clin. Cancer Res.* 13:2151-2157; Hino et al., 2010, *Cancer.* 116:1757-1766. Thus, analysis of 196 tumor specimens from patients with renal cell carcinoma found that high tumor expression of PD-L1 was associated with increased tumor aggressiveness and a 4.5-fold increased risk of death (Thompson et al., 2004, *Proc. Natl. Acad. Sci. U.S.A* 101:17174-17179). Ovarian cancer patients with higher expression of PD-L1 had a significantly poorer prognosis than those with lower expression of PD-L1. An inverse correlation was observed between PD-L1 expression and intraepithelial CD8+ T-lymphocyte count, suggesting that PD-L1 on tumor cells may suppress antitumor CD8+ T cells (Hamanishi et al., 2007, vide supra).

Dendritic cells (DCs) are the most potent antigen-presenting cells, and they have been shown to effectively stimulate specific immune responses.[1] DC vaccines are generally composed of peripheral blood monocytes that are matured into DCs and pulsed with antigens in vitro before they are injected. DC-based cancer vaccines have received much attention over the last decade. However, although many DC vaccination trials have been conducted, clinical benefit has been limited for the majority of patients. With current vaccination strategies, the induced T cell frequencies are not impressive and additional measures are needed to help increase T cell response. Thus, further research is required to optimize the generation and phenotype of DCs to enhance their capacity to induce "fully armored" T cells, to determine the best route of administration, and to identify ideal combinations with additional therapies.

Programmed death 1 (PD-1) is an inhibitory molecule that is expressed on the surface of T cells. The PD-1 ligand PD-L1 (also known as CD274 or B7-H1) is constitutively expressed on lymphoid cells such as monocytes, DCs, and T cells, and it is also present on nonhematopoietic cells, such as endothelial and epithelial cells.[2, 3] PD-L1 can be upregulated by type I and II interferons (IFNs) through IFN regulatory factor-1 (IRF-1) in what appears to be a JAK/STAT-dependent manner. 4 In general, interactions between PD-1 on T cells and PD-L1 control the induction and maintenance of peripheral cell tolerance during normal immune responses. 5 PD-L1 is a critical negative regulator of self-reactive T cells during both the induction and effector phases of autoimmune disease, and it exerts its inhibitory function in multiple ways. In addition to being a ligand for PD-1, PD-L1 binds B7-1 (CD80), preventing B7-1 co-stimulation. IL-10 is produced upon ligation of PD-L1 and possibly augments apoptosis of activated T cells.[6] The immune system is continually looking for foreign pathogens and irregular cells, such as cancer cells. Consequently, in order for cancer to continue to grow, it must hide from the immune system to avoid destruction. PD-1 and its ligands play a central role in maintaining peripheral tolerance and preventing autoimmunity, and cancer cells can exploit this system to create a suppressing microenvironment, thus protecting themselves from immune-mediated killing. Indeed, PD-L1 expression has been found to be high in multiple cancers,[7, 8] and PD-L1 expression was first described as an indicator of tumor aggressiveness in renal cell carcinoma. 9 In addition, PD-L1 expression on tumor cells has been suggested as a prognostic factor in a number of solid cancers, including ovarian and pancreatic cancer. [10, 11]

Blockade of either PD-1 or PD-L1 by monoclonal antibodies has resulted in outstanding clinical responses, [12, 13] and the anti-PD1 antibodies pembrolizumab and nivolumab were recently approved for the treatment of metastatic melanoma by the United States Food and Drug Administration (FDA) (September and December 2014, respectively). The recent discovery of PD-L1-specific T cells suggests that the immune system itself has a mechanism to counteract the effects of PD-1 and its ligand. [14, 15] Indeed, PD-L1-specific T cell responses in peripheral blood were shown to occur at higher frequencies in cancer patients than in healthy donors. [14, 15] Subsequently, these PD-L1-specific T cells were found to lyse PD-L1-expressing cells, including melanoma cells and nonmalignant DCs. [14, 16] In addition, activation of PD-L1-specific T cells boosts the immune response toward viral antigens. [17] These findings suggest an autoreactive function for PD-L1-specific T cells in immune homeostasis. Furthermore, it implies that stimulation with PD-L1-derived peptides can boost a previously existing or vaccine-generated immune response by pushing the immune balance in the microenvironment toward less immune inhibition.

We recently conducted a vaccine study in patients with stage IV malignant melanoma (Borch et al., in preparation). In the study, patients were vaccinated with DCs transfected with mRNA encoding the tumor-associated antigens p53, survivin and telomerase (the vaccine is referred to herein as "DCvacc"). However, the clinical benefits were limited and immunological monitoring of the patients revealed that their peripheral blood mononuclear cells (PBMCs) had only limited reactivity toward DCvacc.

SUMMARY OF THE INVENTION

The present inventors have identified new fragments of human PD-L1 (SEQ ID NO:1) which fragments have good solubility, do not aggregate, are not prone for beta-sheet formation and as such are suitable for, for instance, vaccines together with an adjuvant. The PD-L1 peptide fragment of SEQ ID NO. 91 (which is PDlong2 described in WO2013056716, incorporated herein by reference) is quite hydrophobic and very prone for beta-sheet formation and therefore has low solubility. Furthermore, this peptide contains free SH, and must be handled at low pH to prevent dimer formation.

Furthermore, it has been shown (see below) that the PD-L1 peptide fragments SEQ ID NO. 91 and 89 (referred to in WO2013056716 and herein as PDlong2 and PDlong1 respectively) co-stimulation increases immunogenicity of a dendritic cell-based cancer vaccine. Thus, activation of PD-L1-specific T cells by any one of these two PD-L1 peptide fragments may directly modulate immunogenicity of DC vaccines. Addition of PD-L1 epitopes may thus be an easily applicable and attractive option to augment the effectiveness of cancer vaccines and other immunotherapeutic agents. Thus, it is contemplated that a PD-L1 peptide fragment consisting of SEQ ID NO. 91 or a PD-L1 peptide fragment consisting of SEQ ID NO. 89, as well as longer sequences comprising these will have the effect as shown herein.

In one aspect the present invention relates to a PD-L1 peptide fragment, or pharmaceutically acceptable salt thereof, having the formula:

$X^1$VILGAILLCLGVALTFIX$^2$     (SEQ ID NO: 78)

wherein

N-terminal $X^1$ is selected from a group consisting of L, HL, THL, RTHL (SEQ ID NO: 79), ERTHL (SEQ ID NO: 80), NERTHL (SEQ ID NO: 81), or is absent, C-terminal $X^2$ is selected from a group consisting of F, FR, FRL, FRLR (SEQ ID NO: 82),

FRLRK (SEQ ID NO: 83), FRLRKG (SEQ ID NO: 84), FRLRKGR (SEQ ID NO: 85),

FRLRKGRM (SEQ ID NO: 86), FRLRKGRMM (SEQ ID NO: 87), FRLRKGRMMD (SEQ ID NO: 88), or is absent, provided that if X1 is absent, then X2 is not FRLRKG (SEQ ID NO: 84), wherein the C-terminal amino acid also comprises the amide. In other words, the C terminal amino acid may be replaced with its corresponding amide. $X^1$ and $X^2$ may each be independently selected from the available options.

Where the amino acid form of the C terminal residue is present, this may be indicated herein by the notation X—OH, whereas if the amide form is present this may be indicated by the notation X—NH$_2$. If neither notation is used, it will be understood that both amino acid and amide forms of the C terminal residue are encompassed. The peptide of the invention, or the pharmaceutically acceptable salt thereof, may therefore comprise or consist of any one of the amino acid sequences set out in Table A, optionally wherein the C terminal amino acid is replaced with the corresponding amide form.

TABLE A

| Peptide name | SEQ ID No | Sequence | Start pos | End pos |
|---|---|---|---|---|
| | 2 | VILGAILLCLGVALTFI | 242 | 258 |
| | 3 | VILGAILLCLGVALTFIF | 242 | 259 |
| | 4 | VILGAILLCLGVALTFIFR | 242 | 260 |
| | 5 | VILGAILLCLGVALTFIFRL | 242 | 261 |
| | 6 | VILGAILLCLGVALTFIFRLR | 242 | 262 |
| | 7 | VILGAILLCLGVALTFIFRLRK | 242 | 263 |
| | 8 | VILGAILLCLGVALTFIFRLRKGR | 242 | 265 |

TABLE A-continued

| Peptide name | SEQ ID No | Sequence | Start pos | End pos |
|---|---|---|---|---|
| | 9 | VILGAILLCLGVALTFIFRLRKGRM | 242 | 266 |
| | 10 | VILGAILLCLGVALTFIFRLRKGRMM | 242 | 267 |
| | 11 | VILGAILLCLGVALTFIFRLRKGRMMD | 242 | 268 |
| | 12 | LVILGAILLCLGVALTFI | 241 | 258 |
| | 13 | LVILGAILLCLGVALTFIF | 241 | 259 |
| | 14 | LVILGAILLCLGVALTFIFR | 241 | 260 |
| | 15 | LVILGAILLCLGVALTFIFRL | 241 | 261 |
| | 16 | LVILGAILLCLGVALTFIFRLR | 241 | 262 |
| | 17 | LVILGAILLCLGVALTFIFRLRK | 241 | 263 |
| | 18 | LVILGAILLCLGVALTFIFRLRKG | 241 | 264 |
| | 19 | LVILGAILLCLGVALTFIFRLRKGR | 241 | 265 |
| | 20 | LVILGAILLCLGVALTFIFRLRKGRM | 241 | 266 |
| | 21 | LVILGAILLCLGVALTFIFRLRKGRMM | 241 | 267 |
| | 22 | LVILGAILLCLGVALTFIFRLRKGRMMD | 241 | 268 |
| | 23 | HLVILGAILLCLGVALTFI | 240 | 258 |
| | 24 | HLVILGAILLCLGVALTFIF | 240 | 259 |
| | 25 | HLVILGAILLCLGVALTFIFR | 240 | 260 |
| | 26 | HLVILGAILLCLGVALTFIFRL | 240 | 261 |
| | 27 | HLVILGAILLCLGVALTFIFRLR | 240 | 262 |
| | 28 | HLVILGAILLCLGVALTFIFRLRK | 240 | 263 |
| | 29 | HLVILGAILLCLGVALTFIFRLRKG | 240 | 264 |
| | 30 | HLVILGAILLCLGVALTFIFRLRKGR | 240 | 265 |
| | 31 | HLVILGAILLCLGVALTFIFRLRKGRM | 240 | 266 |
| | 32 | HLVILGAILLCLGVALTFIFRLRKGRMM | 240 | 267 |
| | 33 | HLVILGAILLCLGVALTFIFRLRKGRMMD | 240 | 268 |
| | 34 | THLVILGAILLCLGVALTFI | 239 | 258 |
| | 35 | THLVILGAILLCLGVALTFIF | 239 | 259 |
| | 36 | THLVILGAILLCLGVALTFIFR | 239 | 260 |
| | 37 | THLVILGAILLCLGVALTFIFRL | 239 | 261 |
| | 38 | THLVILGAILLCLGVALTFIFRLR | 239 | 262 |
| | 39 | THLVILGAILLCLGVALTFIFRLRK | 239 | 263 |
| | 40 | THLVILGAILLCLGVALTFIFRLRKG | 239 | 264 |
| | 41 | THLVILGAILLCLGVALTFIFRLRKGR | 239 | 265 |
| | 42 | THLVILGAILLCLGVALTFIFRLRKGRM | 239 | 266 |
| | 43 | THLVILGAILLCLGVALTFIFRLRKGRMM | 239 | 267 |
| | 44 | THLVILGAILLCLGVALTFIFRLRKGRMMD | 239 | 268 |
| | 45 | RTHLVILGAILLCLGVALTFI | 238 | 258 |
| | 46 | RTHLVILGAILLCLGVALTFIF | 238 | 259 |

TABLE A-continued

| Peptide name | SEQ ID No | Sequence | Start pos | End pos |
|---|---|---|---|---|
| | 47 | RTHLVILGAILLCLGVALTFIFR | 238 | 260 |
| | 48 | RTHLVILGAILLCLGVALTFIFRL | 238 | 261 |
| | 49 | RTHLVILGAILLCLGVALTFIFRLR | 238 | 262 |
| | 50 | RTHLVILGAILLCLGVALTFIFRLRK | 238 | 263 |
| | 51 | RTHLVILGAILLCLGVALTFIFRLRKG | 238 | 264 |
| IO104.1 | 52 | RTHLVILGAILLCLGVALTFIFRLRKGR | 238 | 265 |
| | 53 | RTHLVILGAILLCLGVALTFIFRLRKGRM | 238 | 266 |
| | 54 | RTHLVILGAILLCLGVALTFIFRLRKGRMM | 238 | 267 |
| | 55 | RTHLVILGAILLCLGVALTFIFRLRKGRMMD | 238 | 268 |
| | 56 | ERTHLVILGAILLCLGVALTFI | 237 | 258 |
| | 57 | ERTHLVILGAILLCLGVALTFIF | 237 | 259 |
| | 58 | ERTHLVILGAILLCLGVALTFIFR | 237 | 260 |
| | 59 | ERTHLVILGAILLCLGVALTFIFRL | 237 | 261 |
| | 60 | ERTHLVILGAILLCLGVALTFIFRLR | 237 | 262 |
| | 61 | ERTHLVILGAILLCLGVALTFIFRLRK | 237 | 263 |
| | 62 | ERTHLVILGAILLCLGVALTFIFRLRKG | 237 | 264 |
| | 63 | ERTHLVILGAILLCLGVALTFIFRLRKGR | 237 | 265 |
| | 64 | ERTHLVILGAILLCLGVALTFIFRLRKGRM | 237 | 266 |
| | 65 | ERTHLVILGAILLCLGVALTFIFRLRKGRMM | 237 | 267 |
| | 66 | ERTHLVILGAILLCLGVALTFIFRLRKGRMMD | 237 | 268 |
| | 67 | NERTHLVILGAILLCLGVALTFI | 236 | 258 |
| | 68 | NERTHLVILGAILLCLGVALTFIF | 236 | 259 |
| | 69 | NERTHLVILGAILLCLGVALTFIFR | 236 | 260 |
| | 70 | NERTHLVILGAILLCLGVALTFIFRL | 236 | 261 |
| | 71 | NERTHLVILGAILLCLGVALTFIFRLR | 236 | 262 |
| | 72 | NERTHLVILGAILLCLGVALTFIFRLRK | 236 | 263 |
| | 73 | NERTHLVILGAILLCLGVALTFIFRLRKG | 236 | 264 |
| | 74 | NERTHLVILGAILLCLGVALTFIFRLRKGR | 236 | 265 |
| | 75 | NERTHLVILGAILLCLGVALTFIFRLRKGRM | 236 | 266 |
| | 76 | NERTHLVILGAILLCLGVALTFIFRLRKGRMM | 236 | 267 |
| | 77 | NERTHLVILGAILLCLGVALTFIFRLRKGRMMD | 236 | 268 |

The "Start pos" and "End pos" columns indicate the starting position and the ending position of each peptide within the sequence of SEQ ID NO: 1. As will be appreciated from the table, the peptides of the invention comprise or consists of between 17 and 33 consecutive amino acids of the PD-L1 sequence of SEQ TD NO: 1. As described herein, additional residues may be added at the N and/or C termini to improve stability. The consecutive amino acids of SEQ TD NO: 1 preferably comprise at least the amino acids corresponding to positions 242 to 258 of SEQ ID NO: 1, with up to 10 additional amino acids at the C terminal end corresponding to positions 259 to 268 of SEQ TD NO: 1; and/or up to 6 additional amino acids at the N terminal end corresponding to positions 236 to 241 of SEQ TD NO: 1. Particularly preferred is the peptide which comprises or consists of the amino acid sequence RTTILVTL-GATLLCLGVALTFJFRLRKGR (SEQ ID NO: 52), which corresponds to positions 238 to 265 of SEQ ID NO: 1. This peptide may be referred to herein as IO104.1. The C terminal residue of this sequence may be replaced with the corresponding amide form and be equally preferred. The fragment with C terminal amino acid may be referred to as IO104.1-OH. The fragment with C terminal amide may be referred to herein as IO104.1-NH$_2$. One, two, three, four or five conservative substitutions may be made to any one of the sequences of Table A and the resulting sequence still be considered a peptide of the invention, although said peptide is preferably capable of recognition by T cells specific for the HLA-A2 epitope entitled PDL111 (sequence provided as SEQ NO: 92). Most preferably, said conservative substitutions do not alter the amino acids corresponding to positions 250 to 258 of SEQ ID NO: 1, which are the amino acid sequence of the PDL111 epitope.

In one embodiment the peptide fragment of the present invention is selected from NERTHLVILGAILLCLGVALTFIFRLRKGRMMD (SEQ ID NO: 77),
- NERTHLVILGAILLCLGVALTFIFRLRKGRMMD-NH$_2$ (SEQ ID NO: 77 with C terminal amide),
- RTHLVILGAILLCLGVALTFIFRLRKGR (SEQ ID NO: 52),
- RTHLVILGAILLCLGVALTFIFRLRKGR-NH$_2$ (SEQ ID NO: 52 with C terminal amide),
- NERTHLVILGAILLCLGVALTFI (SEQ ID NO: 67)
- NERTHLVILGAILLCLGVALTFI-NH$_2$ (SEQ ID NO: 67 with C terminal amide),
- VILGAILLCLGVALTFI (SEQ ID NO: 2),
- VILGAILLCLGVALTFI-NH$_2$ (SEQ ID NO: 2 with C terminal amide), or
- a pharmaceutically acceptable salt thereof. Typically, the peptide fragment is selected from NERTHLVILGAILLCLGVALTFIFRLRKGRMMD (SEQ ID NO: 77),
- RTHLVILGAILLCLGVALTFIFRLRKGR (SEQ ID NO: 52), and
- RTHLVILGAILLCLGVALTFIFRLRKGR-NH$_2$ (SEQ ID NO: 52 with C terminal amide).

In a further aspect the present invention relates to a composition comprising the PD-L1 peptide fragment of the present invention; optionally together with a pharmaceutically acceptable additive.

In a still further aspect the present invention relates to an immunotherapeutic composition, such as a vaccine, comprising
a) the PD-L1 peptide fragment of the present invention; and
b) an adjuvant;
for use as a medicament.

In an embodiment the immunotherapeutic composition of the present invention is for use in a method for treatment or prevention of a disease, disorder or condition selected from cancer, such as a tumor forming cancer disease; an infection, such as an infectious disease, e.g. an intracellular infection, for example an intracellular infection with a pathogen selected from the group consisting of *L. monocytogenes* and *plasmodium*, a viral infection, for example an infection with a virus selected from the group consisting of HIV and hepatitis; an autoimmune disease, such as diabetes, SLE and sclerosis.

In a further embodiment the adjuvant is selected from the group consisting of bacterial DNA based adjuvants, oil/surfactant based adjuvants, viral dsRNA based adjuvants, imidazochinilines, a Montanide ISA adjuvant.

In a further aspect the present invention relates to a kit-of-parts comprising:
a) the immunotherapeutic composition of the present invention, and
b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine. In an embodiment the provided compositions are to be administered simultaneously or sequentially.

In a still further aspect the present invention relates to a method of treating a clinical condition characterized by expression of PD-L1, the method comprising administering to an individual suffering from said clinical condition an effective amount of the peptide fragment of the present invention, the composition of the present invention, or the kit-of-parts of the present invention.

In a further aspect the present invention relates to use of a peptide fragment of the present invention for the manufacture of a medicament, such as an immunotherapeutic composition or vaccine, for the treatment or prevention of a clinical condition characterized by expression of PD-L1. In one embodiment the clinical condition to be treated is a cancer disease where PD-L1 is expressed. In another embodiment the clinical condition is selected from the group consisting of infectious diseases and autoimmune diseases.

In a still further aspect the present invention relates to a PD-L1 peptide fragment having the formula:

$$X^1VILGAILLCLGVALTFIX^2 \quad \text{(SEQ ID NO: 78)}$$

wherein
N-terminal $X^1$ is selected from a group consisting of L, HL, THL, RTHL (SEQ ID NO: 79), ERTHL (SEQ ID NO: 80), NERTHL (SEQ ID NO: 81), or is absent,
C-terminal $X^2$ is selected from a group consisting of F, FR, FRL, FRLR (SEQ ID NO: 82),
FRLRK (SEQ ID NO: 83), FRLRKG (SEQ ID NO: 84), FRLRKGR (SEQ ID NO: 85),
FRLRKGRM (SEQ ID NO: 86), FRLRKGRMM (SEQ ID NO: 87), FRLRKGRMMD (SEQ ID NO: 88), or is absent,
provided that if X1 is absent, then X2 is not FRLRKG (SEQ ID NO: 84),
wherein the C-terminal amino acid also comprises the amide, or
a pharmaceutically acceptable salt thereof;
for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells. The PD-L1 peptide fragment may be selected from any of those disclosed in Table A, or a pharmaceutically acceptable salt thereof, optionally wherein the C terminal amino acid is replaced with the corresponding amide form. In an embodiment the PD-L1 peptide fragment is selected from NERTHLVILGAILLCLGVALTFIFRLRKGRMMD (SEQ ID NO: 77), NERTHLVILGAILLCLGVALTFIFRLRKGRMMD-NH2 (SEQ ID NO: 77 with C terminal amide),
RTHLVILGAILLCLGVALTFIFRLRKGR (SEQ ID NO: 52),
RTHLVILGAILLCLGVALTFIFRLRKGR-NH$_2$(SEQ ID NO: 52 with C terminal amide),
NERTHLVILGAILLCLGVALTFI (SEQ ID NO: 67),
NERTHLVILGAILLCLGVALTFI-NH$_2$ (SEQ ID NO: 67 with C terminal amide),
VILGAILLCLGVALTFI (SEQ ID NO: 2),
VILGAILLCLGVALTFI-NH$_2$(SEQ ID NO: 2 with C terminal amide), or
a pharmaceutically acceptable salt thereof. Typically, the peptide fragment is selected from NERTHLVIL-GAILLCLGVALTFIFRLRKGRMMD (SEQ ID NO: 77),
RTHLVILGAILLCLGVALTFIFRLRKGR (SEQ ID NO: 52), and
RTHLVILGAILLCLGVALTFIFRLRKGR-NH$_2$ (SEQ ID NO: 52 with C terminal amide).

In a further aspect the present invention relates to a PD-L1 peptide fragment comprising the formula:
FMTYWHLLNAFTVTVPKDL (SEQ ID NO: 89) wherein the C-terminal amino acid also comprises the amide, or a pharmaceutically acceptable salt thereof,
for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells. In an embodiment the PD-L1 peptide fragment is selected from the PD-L1 fragment having the formula: FMTY-WHLLNAFTVTVPKDL (SEQ ID NO: 89) wherein the C-terminal amino acid also comprises the amide. In a further embodiment the additional cancer therapy is selected from an immune system checkpoint inhibitor, wherein the inhibitor is a checkpoint blocking antibody selected from Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

DESCRIPTION OF DRAWINGS

FIG. 1A-FIG. 1I. Costimulation with PD-L1-derived epitopes enhance the frequency of T cells reactive against dendritic cell vaccine. (FIG. 1A) PBMCs (5×10$^6$) from patients were stimulated twice in vitro with DCvacc. The following day, the cultures were costimulated with one or two long PD-L1 epitopes or incubated with an irrelevant HIV control peptide. All cultures were stimulated with IL2 the day after peptide stimulation. Cultures were examined for DCvacc-reactive T cells after 16-20 days by intracellular TNFα/INFγ staining. (FIG. 1B-FIG. 1I) Examples of PBMC cultures from three melanoma patients in which co-activation of PD-L1 specific T cells significantly boosted T cell immunity toward DCvacc, as measured by intracellular TNFα/INFγ staining. (FIG. 1B) CD4$^+$ T cells released only TNFα in response to DCvacc. (FIG. 1C) % cytokine released by CD4$^+$ T cells in four conditions presented in FIG. 1B. (FIG. 1D) PD-L1 peptide costimulation induced TNFα/INFγ double-positive CD4$^+$ T cells in response to DCvacc. (FIG. 1E) % cytokine released by CD4$^+$ T cells in four conditions presented in FIG. 1D. (FIG. 1F, FIG. 1H) Costimulation with PD-L1 epitopes increased the number of both CD4+ and CD8$^+$ cells that reacted against DCvacc. (FIG. 1G, FIG. 1I) % cytokine released by CD4$^+$ T cells in four conditions presented in FIG. 1F and FIG. 1H, respectively.

FIG. 2A) and after four vaccinations (FIG. 2B). Percentages of DCvacc-reactive CD8$^+$ T cells in cultures of PBMCs taken from eight melanoma patients before vaccination (baseline; FIG. 2C) and after four vaccinations (FIG. 2D).

(FIG. 3A) IFNγ ELISPOT was used to measure T cell response towards PDLong1 and PDLong2 in tumor-infiltrating lymphocytes from melanoma patients. In 5×10$^4$ cells from 12 melanoma patients, the average number of IFNα-releasing cells in response to either PDLong1 or PDLong2 was measured. (FIG. 3B) Example of ELISPOT wells performed with TILs from two melanoma patients either without or with PDLong1 or PDLong2 peptides (FIG. 3C) Tumor-infiltrating lymphocytes were cultured for 5 hours either without or with PDLong1 or PDLong2 before being analyzed for intracellular IFNγ/TNFα staining. Example of IFNγ/TNFα staining of tumor-infiltrating lymphocytes from a melanoma patient in response to either without peptide (FIG. 3D) or with PDLong1 (FIG. 3E) or PDLong2 (FIG. 3F).

FIG. 4A-FIG. 4D. Stimulation of patient PBMCs with PDLong1 plus PDLong2 together with a DC vaccine. At days 16-20, after two stimulations with DCvacc and two stimulations with either an irrelevant control peptide or PDLong1 plus PDLong2 peptide, the percentage of cells that released TNFα/INFγ in response to DCvacc was identified by flow cytometry. Percentages of DCvacc-reactive CD4$^+$ T cells in cultures of PBMCs taken from eight melanoma patients before vaccination (baseline; FIG. 4A) and after four vaccinations (FIG. 4B). Percentages of DCvacc-reactive CD8$^+$ T cells in cultures of PBMCs taken from eight melanoma patients before vaccination (baseline; FIG. 4C) and after four vaccinations (FIG. 4D).

FIG. 5A) and after four vaccinations (FIG. 5B), (2) the presence of IL-6 could be measured before vaccination (baseline; FIG. 5C) and after four vaccinations (FIG. 5D), and (3) the presence of TFGβ could be measured before vaccination (baseline; FIG. 5E) and after four vaccinations (FIG. 5F). In addition, the total numbers of cells were counted after the second stimulation with either HIV or PDLong1 plus PDLong2 epitopes before vaccination (baseline; FIG. 5G) and after four vaccinations (FIG. 5H).

FIG. 8A shows the timeline for the experiment described in Example 3; (FIG. 8B) Elispot results for sple-nocytes stimulated with one of 5 peptide candidates ex vivo; Representative Elispot wells (FIG. 8C) and results (FIG. 8D) for splenocytes stimulated with the most effective peptide (mLong1). n=5-10 mice/group.

FIG. 9A shows the timeline for the experiment described in Example 4; Elispot results for cells from the spleen (FIG. 9B) and dLNs (FIG. 9C) was stimulated with mPD-L1 long1 or mPD-L1 short ex vivo; (FIG. 9D) Representative Elispot wells of one of the DNFB treated mice with highest response compared to a control. n=12 mice/group FIG. 10A-FIG. 10C. Vaccination with mPD-L1long1 expands the population of PD-L1-specific T cells in mice.

FIG. 11A shows the timeline for the experiment described in Example 6; (FIG. 11B) Change in tumor volume over time for each mouse (M1-M3 vaccinated with Montanide only; M4-M5 vaccinated with mPD-L1long1 plus Montanide); (FIG. 11C) Kaplan-Meier survival curve; (FIG. 11D) Change in mean tumor volume over time for each group. n=3 mice/group.

DESCRIPTION OF SEQUENCES

Figure 1A:
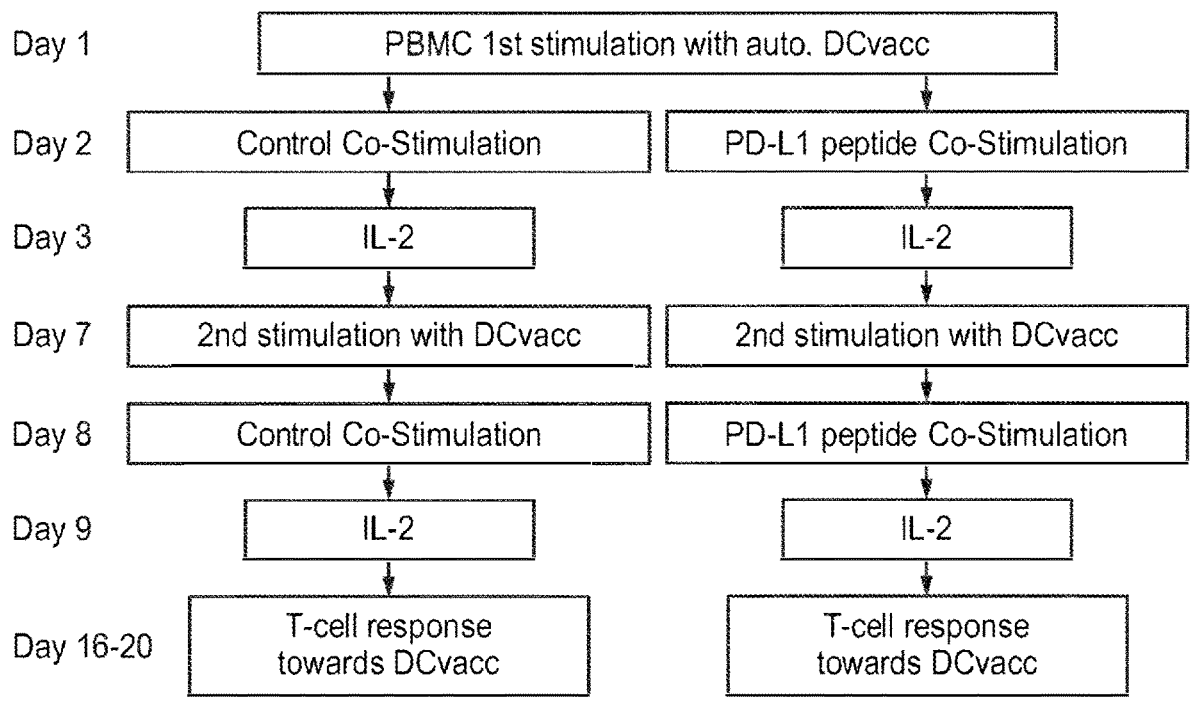
Figure 1F:
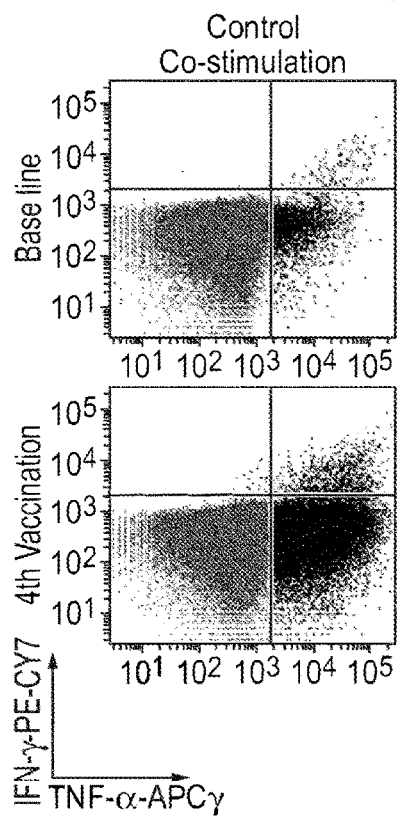
Figure 1G:
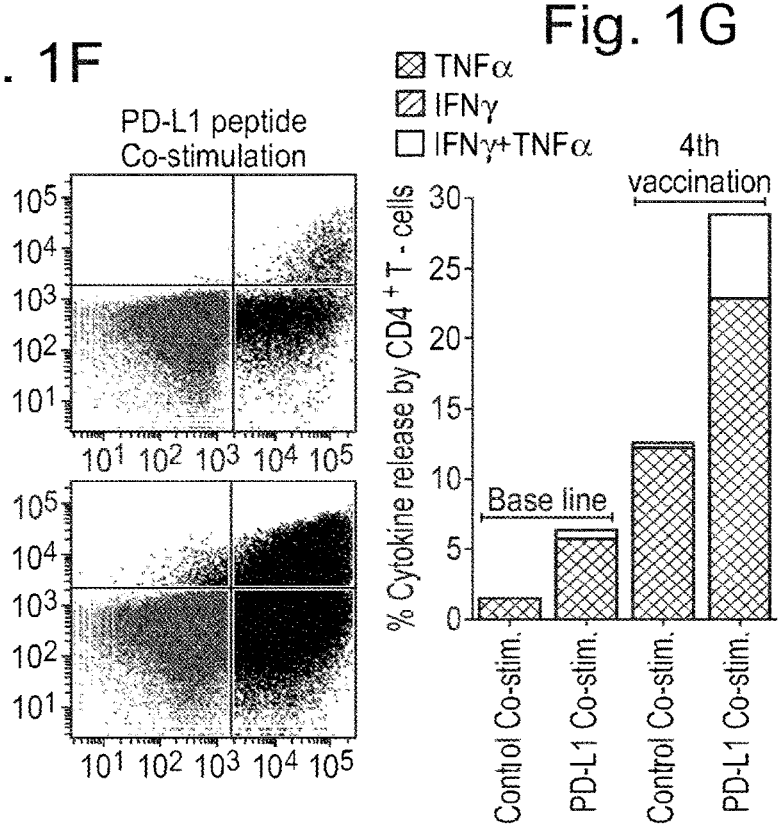
Figure 1H:
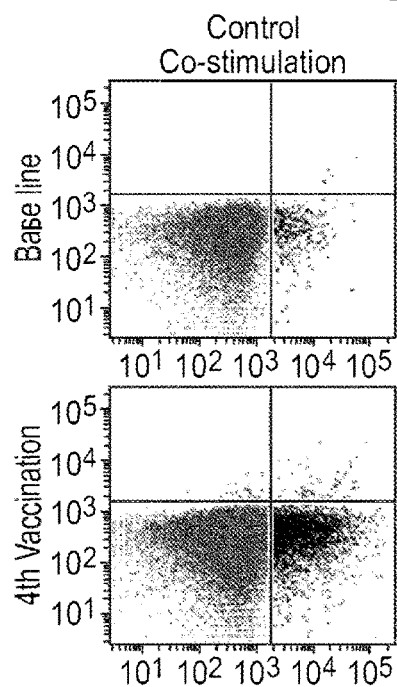
Figure 1I:
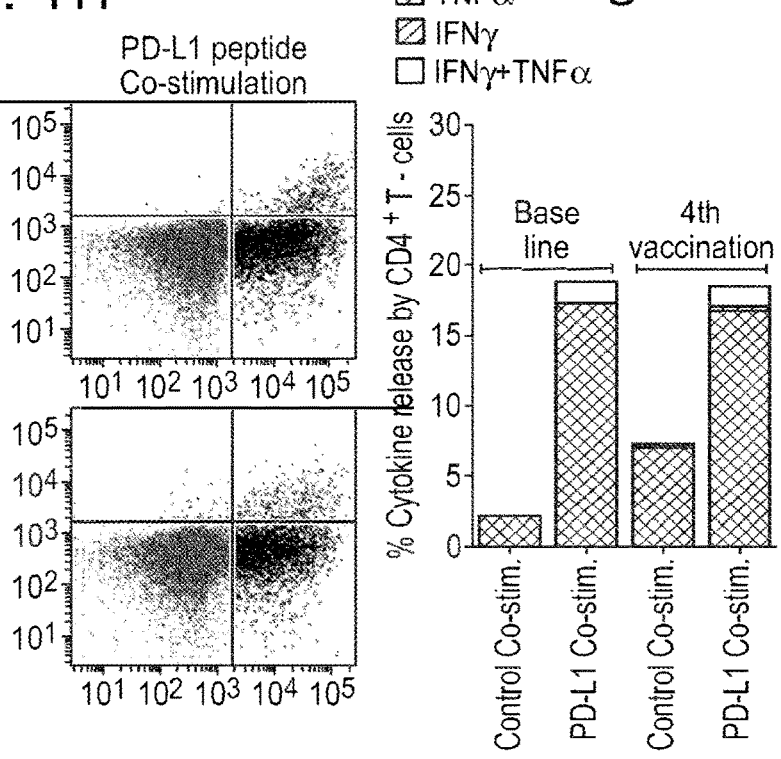

SEQ ID NO: 1 is the full length amino acid sequence of human (h)PD-L1

SEQ ID NOs: 2 to 77 are the amino acid sequences of exemplary peptides of the invention, all of which are fragments of hPD-L1.

SEQ ID NO: 78 is an amino acid sequence representing a general formula corresponding to the peptides of the invention.

SEQ ID NOs: 79 to 81 are various N terminal amino acid sequences which may be added to the formula of SEQ ID NO: 78.

SEQ ID NOs: 82 to 88 are various C terminal amino acid sequences which may be added to the formula of SEQ ID NO: 78.

SEQ ID NO: 89 is another exemplary peptide of the invention, being a fragment of hPD-L1

SEQ ID NO: 90 is a T cell epitope sequence comprised within SEQ ID NO: 89.

SEQ ID NO: 91 is the amino acid sequence of a fragment of hPDL1 which is disclosed herein SEQ ID NO: 92 is the amino acid sequence of the HLA-A2 epitope entitled PDL111 (corresponds positions 250-258 of hPDL1), SEQ ID NOs: 93 and 94 are the amino acid sequence of certain peptides used as controls in the Examples.

SEQ ID NO: 95 is the full length amino acid sequence of murine (m)PD-L1.

SEQ ID NOs: 96 to 100 are the amino acid sequences of peptides derived from mPD-L1 which are used as analogs for the peptides of the invention in the mouse model experiments described in the Examples.

SEQ ID NO: 101 is a T cell epitope sequence comprised within SEQ ID NO: 96.

DETAILED DESCRIPTION OF THE INVENTION

The problem of cancer immunosuppression was solved in WO2013056716 wherein PD-L1 fragments of human PD-L1 full length (SEQ ID NO. 1) was based on the surprising finding by the inventors of spontaneous cytotoxic immune responses against PD-L1 expressing cells in cancer patients. These findings open the way for novel therapeutic and diagnostic approaches which may be generally applicable in the control of cancer diseases. Interestingly, the findings are not restricted to cancer but are also useful in other clinical conditions characterized by the presence of undesired cells expressing PD-L1.

The invention disclosed in WO2013056716 targets the cancer disease by killing the PD-L1 expressing cancer cells directly and by killing the PD-L1 expressing regulatory cells. This is done by enabling the T cells to recognize the PD-L1 expressing cells. Likewise, when the clinical condition is an infection, T cells are enabled to kill PD-L1 expressing APCs/DCs. Thus, the expression of the immune suppressing enzyme PD-L1 in cancer cells and APCs is positive in conjunction with the application of the method of the present invention, which targets these PD-L1 expressing cells. This approach, especially as it entails the killing of the APCs/DCs, goes against the common opinion in the field, where PD-L1 generally is attempted inhibited in order to remove the tolerating milieu around the APCs/DCs while preserving these cells, which are considered required in order to launch an effective immune response. Furthermore, the finding of spontaneous cytotoxic immune responses against PD-L1 expressing cells is particularly surprising since PD-L1 expressing cells antagonize the desired effects of other immunotherapeutic approaches. Therefore, a combination of PD-L1- and tumor-targeting immunotherapies is highly synergistic. The presence of an in vivo T-cell response specific for PD-L1 demonstrates that cancer patients are capable of generating T-cell responses to PD-L1 in vivo in response to the presence of PD-L1 peptides. Thus, the two conditions for generating a T-cell response are met: The T cells are present in the cancer patient and they have the ability to expand, which are shown in the application as filed. It follows from the general knowledge in the field of immunology that providing additional PD-L1 protein or PD-L1 peptides will lead to generation of PD-L1 specific T-cell responses. In contrast to membrane-bound antibodies on B cells, which can recognize antigen alone, the T-cells recognizes a complex ligand, comprising an antigenic peptide bound to a protein called the major histocompatibility complex (MHC). In man, this molecule is known as human leukocyte antigen (HLA). Class I HLA molecules sample peptides from protein-degradation inside the cell and present these at the cell surface to T cells. Hence, this enables T-cells to scan for cellular alterations. When a T cell encounters antigen in the context of a HLA molecule, it undergoes clonal expansion and differentiates into memory and various effector T cells. Hence, identification of a spontaneous immune response is evidence that an antigen is a T-cell target. It demonstrates that specific T-cells have already been activated and have expanded in vivo.

The PD-L1 peptide fragment of SEQ ID NO. 91 (described in WO2013056716 as PDLong2) is quite hydrophobic and very prone for beta-sheet formation and therefore has low solubility. Furthermore, this peptide contains free SH, and must be handled at low pH to prevent dimer formation. Hence, there is a need for a more soluble and easy to handle PD-L1 peptide fragment comprising the amino acid sequence of SEQ ID NO. 91 or at least a part of that sequence lacking up to 6 amino acids from the C-terminal.

In a broad aspect the present invention relates to a PD-L1 peptide fragment having the formula:

$X^1$VIILGAILLCLGVALTFI$X^2$ (SEQ ID NO: 78)

wherein

N-terminal $X^1$ is selected from a group consisting of L, HL, THL, RTHL (SEQ ID NO: 79), ERTHL (SEQ ID NO: 80), NERTHL (SEQ ID NO: 81), or is absent, C-terminal $X^2$ is selected from a group consisting of F, FR, FRL, FRLR (SEQ ID NO: 82), FRLRK (SEQ ID NO: 83), FRLRKG (SEQ ID NO: 84), FRLRKGR (SEQ ID NO: 85), FRLRKGRM (SEQ ID NO: 86), FRLRKGRMM (SEQ ID NO: 87), FRLRKGRMMD (SEQ ID NO: 88), or is absent, provided that if X1 is absent, then X2 is not FRLRKG (SEQ ID NO: 84), wherein the C-terminal amino acid also comprises the amide, or a pharmaceutically acceptable salt thereof. The PD-L1 peptide fragment may be selected from any of those disclosed in Table A, or a pharmaceutically acceptable salt thereof, optionally wherein the C terminal amino acid is replaced with the corresponding amide form. As used herein any amino acid sequence shown may be modified at the C-terminal amino acid to be on amide form (—CONH$_2$) or may be on acid form (—COOH), thus any one of these are preferred embodiments, and it is intended that any C-terminal amino acid, such as I, F, R, L, K, G, M, D comprises both amide and acid form unless specified by —NH$_2$ or —OH.

In a further embodiment $X^1$ is selected from the group consisting of RTHL (SEQ ID NO: 79) and NERTHL (SEQ ID NO: 81).

In a still further embodiment $X^2$ is selected from the group consisting of FRLRKGR-OH (SEQ ID NO: 85), FRLRKGR-NH$_2$ (SEQ ID NO: 85 with C terminal amide) and FRLRKGRMMD-OH (SEQ ID NO: 88).

In one embodiment the peptide fragment of the present invention is selected from NERTHLVILGAILLCLGVALTFIFRLRKGRMMD-OH (SEQ ID NO: 77),
NERTHLVILGAILLCLGVALTFIFRLRKGRMMD-NH$_2$ (SEQ ID NO: 77 with C terminal amide),
RTHLVILGAILLCLGVALTFIFRLRKGR-OH (SEQ ID NO: 52),
RTHLVILGAILLCLGVALTFIFRLRKGR-NH$_2$ (SEQ ID NO: 52 with C terminal amide),
NERTHLVILGAILLCLGVALTFI-OH (SEQ ID NO: 67),
NERTHLVILGAILLCLGVALTFI-NH$_2$ (SEQ ID NO: 67 with C terminal amide),
VILGAILLCLGVALTFI-OH (SEQ ID NO: 2),
VILGAILLCLGVALTFI-NH$_2$(SEQ ID NO: 2 with C terminal amide), or a pharmaceutically acceptable salt thereof. Typically, the peptide fragment is selected from

```
                                         (SEQ ID NO: 77)
NERTHLVILGAILLCLGVALTFIFRLRKGRMMD-OH, (SEQ ID NO: 52)
RTHLVILGAILLCLGVALTFIFRLRKGR-OH,
and (SEQ ID NO: 52 with C terminal amide)
RTHLVILGAILLCLGVALTFIFRLRKGR-NH2.
```

In a further aspect the present invention relates to a composition comprising the PD-L1 peptide fragment of the present invention; optionally together with a pharmaceutically acceptable additive. In further embodiments the PD-L1 peptide fragment of the present invention is selected form any one of the above in relation to the broad aspect. Typically, a pharmaceutically acceptable additive is present. In an embodiment the composition is a vaccine composition. In a further embodiment the additive is selected from carriers, excipients, diluents, and adjuvants, typically adjuvants. Such adjuvants may be selected form the group consisting of bacterial DNA based adjuvants, oil/surfactant based adjuvants, viral dsRNA based adjuvants, imidazochinilines, a Montanide ISA adjuvant.

In a still further aspect the present invention relates to an immunotherapeutic composition comprising
a) the PD-L1 peptide fragment of the present invention; and
b) an adjuvant;
for use as a medicament. In further embodiments the PD-L1 peptide fragment of the present invention is selected form any one of the above in relation to the broad aspect. In further embodiments the adjuvants may be selected form the group consisting of bacterial DNA based adjuvants, oil/surfactant based adjuvants, viral dsRNA based adjuvants, imidazochinilines, a Montanide ISA adjuvant. Each of these adjuvants or group of adjuvants constitute an individual embodiment.

In an embodiment the immunotherapeutic composition of the present invention is for use in a method for treatment or prevention of a disease, disorder or condition selected from cancer, such as a tumor forming cancer disease; an infection, such as an infectious disease, e.g. an intracellular infection, for example an intracellular infection with a pathogen selected from the group consisting of *L. monocytogenes* and *plasmodium*, a viral infection, for example an infection with a virus selected from the group consisting of HIV and hepatitis; an autoimmune disease, such as diabetes, SLE and sclerosis. Each of the disease, disorder or condition or group of disease, disorder or condition constitute an individual embodiment.

In a further aspect the present invention relates to a kit-of-parts comprising:
a) the immunotherapeutic composition of the present invention, and
b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine. In an embodiment the provided compositions are to be administered simultaneously. In another embodiment the provided compositions are to be administered sequentially. In respect of the immunotherapeutic composition under a) further embodiments of the PD-L1 peptide fragment of the present invention is selected form any one of the above in relation to the broad aspect. In further embodiments the adjuvants may be selected form the group consisting of bacterial DNA based adjuvants, oil/surfactant based adjuvants, viral dsRNA based adjuvants, imidazochinilines, a Montanide ISA adjuvant. Each of these adjuvants or group of adjuvants constitute an individual embodiment. In respect of the second active ingredient under b) further embodiments of the second active ingredient is selected form any one of the above which constitutes individual embodiments.

In a further aspect the present invention relates to a kit-of-parts comprising:
a) the immunotherapeutic composition of the present invention, and
b) an immunomodulatory agent which blocks or inhibits an immune system checkpoint, which checkpoint may be the same as, or different from, the checkpoint of which the composition of (a) comprises a component. In other words, it may be the same as, or different from, the checkpoint which comprises the interaction between PD1 and PDL1.

In an embodiment the checkpoint is selected from the following:
a) The interaction between IDO1 and its substrate;
b) The interaction between PD1 and PDL1 and/or PD1 and PDL2;
c) The interaction between CTLA4 and CD86 and/or CTLA4 and CD80;
d) The interaction between B7-H3 and/or B7-H4 and their respective ligands;
e) The interaction between HVEM and BTLA;
f) The interaction between GAL9 and TIM3;
g) The interaction between MHC class I or II and LAG3; and
h) The interaction between MHC class I or II and KIR In a further embodiment the immunomodulatory agent is an antibody or small molecule inhibitor (SMI) which binds to a component of a said immune system checkpoint.

In a further embodiment the agent is a small molecule inhibitor of IDO1, optionally wherein said inhibitor is Epacadostat (INCB24360), Indoximod, GDC-0919 (NLG919) or F001287, or wherein said agent is an antibody which binds to CTLA4 or PD1, optionally wherein said antibody which binds to CTLA4 is ipilimumab and said antibody which binds to PD1 is pembrolizumab.

In a still further aspect the present invention relates to a method of treating a clinical condition characterized by expression of PD-L1, the method comprising administering to an individual suffering from said clinical condition an effective amount of the peptide fragment of the present invention, the composition of the present invention, or the kit-of-parts of the present invention.

In a still further aspect the present invention relates to a method of treating a clinical condition characterized by expression of PD-L1, the method comprising administering to an individual suffering from said clinical condition an effective amount of a PD-L1 peptide fragment having the formula:

$X^1$VILGAILLCLGVALTFIX$^2$ (SEQ ID NO: 78)

wherein
N-terminal $X^1$ is selected from a group consisting of L, HL, THL, RTHL (SEQ ID NO: 79), ERTHL (SEQ ID NO: 80), NERTHL (SEQ ID NO: 81), or is absent,
C-terminal $X^2$ is selected from a group consisting of F, FR, FRL, FRLR (SEQ ID NO: 82),
FRLRK (SEQ ID NO: 83), FRLRKG (SEQ ID NO: 84), FRLRKGR (SEQ ID NO: 85),
FRLRKGRM (SEQ ID NO: 86), FRLRKGRMM (SEQ ID NO: 87), FRLRKGRMMD (SEQ ID NO: 88), or is absent,
provided that if X1 is absent, then X2 is not FRLRKG (SEQ ID NO: 84),
wherein the C-terminal amino acid also comprises the amide, or
a pharmaceutically acceptable salt thereof. The PD-L1 peptide fragment may be selected from any of those disclosed in Table A, or a pharmaceutically acceptable salt thereof, optionally wherein the C terminal amino acid is replaced with the corresponding amide form.

In a further aspect the present invention relates to use of a PD-L1 peptide fragment of the present invention for the manufacture of a medicament, such as an immunotherapeutic composition or vaccine, for the treatment or prevention of a clinical condition characterized by expression of PD-L1. In an embodiment of the use of a peptide fragment of the present invention the medicament is an immunotherapeutic composition. In another embodiment of the use of a peptide fragment of the present invention the medicament is vaccine. In one embodiment the clinical condition to be treated is a cancer disease where PD-L1 is expressed. In another embodiment the clinical condition is selected from the group consisting of infectious diseases and autoimmune diseases. In a further embodiment the PD-L1 peptide fragment has the formula:

$X^1$VILGAILLCLGVALTFIX$^2$ (SEQ ID NO: 78)

wherein
N-terminal $X^1$ is selected from a group consisting of L, HL, THL, RTHL (SEQ ID NO: 79),
ERTHL (SEQ ID NO: 80), NERTHL (SEQ ID NO: 81), or is absent,
C-terminal $X^2$ is selected from a group consisting of F, FR, FRL, FRLR (SEQ ID NO: 82),
FRLRK (SEQ ID NO: 83), FRLRKG (SEQ ID NO: 84), FRLRKGR (SEQ ID NO: 85),
FRLRKGRM (SEQ ID NO: 86), FRLRKGRMM (SEQ ID NO: 87), FRLRKGRMMD (SEQ ID NO: 88), or is absent,
provided that if X1 is absent, then X2 is not FRLRKG (SEQ ID NO: 84),
wherein the C-terminal amino acid also comprises the amide, or
a pharmaceutically acceptable salt thereof. The PD-L1 peptide fragment may be selected from any of those disclosed in Table A, or a pharmaceutically acceptable salt thereof, optionally wherein the C terminal amino acid is replaced with the corresponding amide form.

In a still further aspect the present invention relates to a PD-L1 peptide fragment having the formula:

$X^1$VILGAILLCLGVALTFIX$^2$ (SEQ ID NO: 78)

wherein

N-terminal X¹ is selected from a group consisting of L, HL, THL, RTHL (SEQ ID NO: 79),
ERTHL (SEQ ID NO: 80), NERTHL (SEQ ID NO: 81), or is absent,
C-terminal X² is selected from a group consisting of F, FR, FRL, FRLR (SEQ ID NO: 82),
FRLRK (SEQ ID NO: 83), FRLRKG (SEQ ID NO: 84), FRLRKGR (SEQ ID NO: 85),
FRLRKGRM (SEQ ID NO: 86), FRLRKGRMM (SEQ ID NO: 87), FRLRKGRMMD (SEQ ID NO: 88), or is absent,
provided that if X1 is absent, then X2 is not FRLRKG (SEQ ID NO: 84),
wherein the C-terminal amino acid also comprises the amide, or
a pharmaceutically acceptable salt thereof;
for use in a method for treatment or prevention of a cancer, when administered simultaneously or sequentially with an additional cancer therapy. The PD-L1 peptide fragment may be selected from any of those disclosed in Table A, or a pharmaceutically acceptable salt thereof, optionally wherein the C terminal amino acid is replaced with the corresponding amide form. The additional cancer therapy may be a cytokine therapy, a T-cell therapy, an NK therapy, an immune system checkpoint inhibitor, chemotherapy, radiotherapy, immunostimulating substances, gene therapy, antibodies and dendritic cells. Each of the additional cancer therapies that is a cytokine therapy, a T-cell therapy, an NK therapy, an immune system checkpoint inhibitor, chemotherapy, radiotherapy, immunostimulating substances, gene therapy, antibodies and dendritic cells constitutes individual embodiments. For instance, in a further embodiment the additional cancer therapy is selected from an immune system checkpoint inhibitor, wherein the inhibitor is a checkpoint blocking antibody selected from Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine. In an embodiment the PD-L1 peptide fragment is selected from
NERTHLVILGAILLCLGVALTFIFRLRKGRMMD (SEQ ID NO: 77),
NERTHLVILGAILLCLGVALTFIFRLRKGRMMD-NH₂ (SEQ ID NO: 77 with C terminal amide),
RTHLVILGAILLCLGVALTFIFRLRKGR (SEQ ID NO: 52),
RTHLVILGAILLCLGVALTFIFRLRKGR-NH₂ (SEQ ID NO: 52 with C terminal amide),
NERTHLVILGAILLCLGVALTFI (SEQ ID NO: 67)
NERTHLVILGAILLCLGVALTFI-NH₂ (SEQ ID NO: 67 with C terminal amide),
VILGAILLCLGVALTFI (SEQ ID NO: 2),
VILGAILLCLGVALTFI-NH₂(SEQ ID NO: 2 with C terminal amide), or
a pharmaceutically acceptable salt thereof. Typically, the peptide fragment is selected from
NERTHLVILGAILLCLGVALTFIFRLRKGRMMD (SEQ ID NO: 77),
RTHLVILGAILLCLGVALTFIFRLRKGR (SEQ ID NO: 52), and
RTHLVILGAILLCLGVALTFIFRLRKGR-NH₂(SEQ ID NO: 52 with C terminal amide).

In a further aspect the present invention relates to a PD-L1 peptide fragment comprising the formula:
FMTYWHLLNAFTVTVPKDL (SEQ ID NO: 89)
wherein the C-terminal amino acid also comprises the amide, or a pharmaceutically acceptable salt thereof,
for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells. In an embodiment the PD-L1 peptide fragment consists of up to 35 consecutive amino acids, such 30, or 25, of the sequence of SEQ ID NO. 1 and comprises the PD-L1 fragment having the formula: FMTYWHLLNAFTVTVPKDL (SEQ ID NO: 89). In an embodiment the PD-L1 peptide fragment is selected from the PD-L1 fragment having the formula: FMTYWHLLNAFTVTVPKDL (SEQ ID NO: 89) wherein the C-terminal amino acid also comprises the amide. In a further embodiment the additional cancer therapy is selected from an immune system checkpoint inhibitor, wherein the inhibitor is a checkpoint blocking antibody selected from Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

The PD-L1 peptide fragments disclosed herein are made by standard peptide synthesis, such as solid-phase peptide synthesis (SPPS). SPPS is a standard method for synthesizing peptides in the lab. SPPS allows for the synthesis of natural peptides which are difficult to express in bacteria, the incorporation of unnatural amino acids, peptide/protein backbone modification, and the synthesis of D-proteins, which consist of D-amino acids. Small porous beads are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process while liquid-phase reagents and by-products of synthesis are flushed away. The general principle of SPPS is one of repeated cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin. There are two majorly used forms of SPPS—Fmoc and Boc. Unlike ribosome protein synthesis, solid-phase peptide synthesis proceeds in a C-terminal to N-terminal fashion. The N-termini of amino acid monomers is protected by either of these two groups and added onto a deprotected amino acid chain. Automated synthesizers are available for both techniques, though many research groups continue to perform SPPS manually. Furthermore, the skilled person will understand that the processes described above and hereinafter the functional groups of intermediate compounds may need to be protected by protecting group.

When the compounds and pharmaceutical compositions herein disclosed are used for the above treatment, a therapeutically effective amount of at least one compound is administered to a mammal in need of said treatment.

As used herein amino acids are identified by the one or three letter code known to the person skilled in the art and shown in the table below for convenience:

Amino Acids, One and Three Letter Codes

| Amino acid | Three letter code | One letter code |
|---|---|---|
| Alanine | ala | A |
| Arginine | arg | R |
| Asparagine | asn | N |
| aspartic acid | asp | D |
| asparagine or aspartic acid | asx | B |
| Cysteine | cys | C |
| glutamic acid | glu | E |
| Glutamine | gln | Q |
| glutamine or glutamic acid | glx | Z |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a PD-L1 peptide fragment of the present invention or a peptide fragment as disclosed herein, as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the PD-L1 peptide fragment of the present invention and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

Adjuvants are any substance whose admixture into the composition increases or otherwise modifies the immune response elicited by the composition. Adjuvants, broadly defined, are substances which promote immune responses. Adjuvants may also preferably have a depot effect, in that they also result in a slow and sustained release of an active agent from the administration site. A general discussion of adjuvants is provided in *Goding, Monoclonal Antibodies: Principles & Practice* (2nd edition, 1986) at pages 61-63.

Adjuvants may be selected from the group consisting of: AlK(SO4)2, AlNa(SO4)2, AlNH4 (SO4), silica, alum, Al(OH)3, Ca3 (P04)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmu-ramyl-L-alanyl-D-isoglutaminyl-L-alanine-2-(1'2'-dipalmitoyl-sn-glycero-3-hydroxphosphor-yloxy)-ethylamine (CGP 19835A, also referred to as MTP-PE), RIBI (MPL+TDM+CWS) in a 2% squalene/Tween-80.RTM. emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in *Corynebacterium parvum, Bordetella pertussis*, and members of the genus *Brucella*, Titermax, ISCOMS, Quil A, ALUN (see US 58767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Various saponin extracts have also been suggested to be useful as adjuvants in immunogenic compositions. Granulocyte-macrophage colony stimulating factor (GM-CSF) may also be used as an adjuvant.

Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. GM-CSF and Imidazochinilines are also examples of preferred adjuvants.

The adjuvant is most preferably a Montanide ISA adjuvant. The Montanide ISA adjuvant is preferably Montanide ISA 51 or Montanide ISA 720.

In *Goding, Monoclonal Antibodies: Principles & Practice* (2nd edition, 1986) at pages 61-63 it is also noted that, when an antigen of interest is of low molecular weight, or is poorly immunogenic, coupling to an immunogenic carrier is recommended. A polypeptide or fragment of an immunotherapeutic composition of the invention may be coupled to a carrier. A carrier may be present independently of an adjuvant. The function of a carrier can be, for example, to increase the molecular weight of a polypeptide fragment in order to increase activity or immunogenicity, to confer stability, to increase the biological activity, or to increase serum half-life. Furthermore, a carrier may aid in presenting the polypeptide or fragment thereof to T-cells. Thus, in the immunogenic composition, the polypeptide or fragment thereof may be associated with a carrier such as those set out below.

The carrier may be any suitable carrier known to a person skilled in the art, for example a protein or an antigen presenting cell, such as a dendritic cell (DC). Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively, the carrier protein may be tetanus toxoid or diphtheria toxoid. Alternatively, the carrier may be a dextran such as sepharose. The carrier must be physiologically acceptable to humans and safe.

The immunotherapeutic composition may optionally comprise a pharmaceutically acceptable excipient. The excipient must be 'acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in *Remington's Pharmaceutical Sciences* (Mack Pub. Co., N.J. 1991).

The immunotherapeutic composition may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e. g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al. (1993) *Pharm. Res.* 10:362-368. Other particulate systems and polymers can also be used, for example, polymers such as polylysine, polyarginine, polyornithine, spermine, spermidine, as well as conjugates of these molecules.

As mentioned above, the compositions and particularly immunotherapetic compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition. Any composition, vaccine, or kit as described herein may additionally comprise a preservative, which may improve the stability of the component peptide fragments of the invention when stored in solution or as a lyophilisate. Suitable preservatives are well known in the art and are preferably pharmaceutically acceptable. In some cases stability of the peptide fragments may be increased by the incorporation of additional terminal residues, at the N terminus, at the C terminus, or at both termini. Such residues would typically be hydrophilic amino acid residues or corresponding amides. Typically the peptide fragments may include an additional 1, 2 or 3 such residues at the N and/or C termini.

In some embodiments, only one compound as herein disclosed is used for the purposes discussed above.

In some embodiments, two or more of the compound as herein disclosed are used in combination for the purposes discussed above.

The composition, particularly immunotherapetic composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'immunotherapetic composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXAMPLES

Example 1

Materials and Methods

Patients and Donors 26 stage IV melanoma patients were enrolled in an open-labeled, non-randomized phase I/II study (EudraCT number 2009-010194-20; Clinicaltrials.gov identifier: NCT00978913). The protocol was approved by the Scientific Ethics Committee for The Capital Region of Denmark (H-A-2009-013), the Danish Medicines Agency (2612-4030), the Danish Data Protection Agency and conducted in accordance with the provisions of the Declaration of Helsinki. Writ-ten informed consent from the patients was obtained before study entry. The clinical and immunological results will be reported elsewhere (Borch et al., in preparation). In short patients were injected with autologous DC vaccines intradermally fortnightly six times and subsequently every four weeks until progression. Concomitantly, patients were treated with a metronomic cyclophosphamide regimen (50 mg twice a day) biweekly.

For immune monitoring purposes Peripheral Blood Mononuclear Cells (PBMC) were collected from patients before vaccination, after four and six vaccinations with a dendritic cell vaccine (DCvacc). PBMC were isolated using Lymphoprep separation, HLA-typed and frozen in FCS with 10% DMSO. DC vaccines were generated as previously described[24] and all procedures were performed according to Good Manufacturing Practice (GMP) as approved by the Danish Medicines Agency. In short, autologous PBMCs were isolated by leukapheresis, and monocytes were further isolated and cultured for 8 days. On day 6, maturation of DCs was performed using IL-1p, TNFα, IL-6, and PGE2. Aliquots of $1\times10^7$ DCs were frozen using automated cryopreservation. The matured DCs were transfected with mRNA encoding the tumor associated antigens p53, survivin and hTERT to generate DCvacc.

Peptides

A 19 amino acid long polypeptide from PD-L1 was synthesized (TAG Copenhagen, Copenhagen, Denmark): PDLong1: $PDL1_{9-28}$ g, FMTYWHLLNAFTVTVPKDL—SEQ ID NO: 89. PDLong1 included sequence of 9mer HLA-A2 restricted peptide (here entitled "PD-L101")

PDL1$_{15-23}$; (LLNAFTVTV—SEQ ID NO: 90) identified and analyzed using the epitope prediction Database "SYFPEITHI" available on the internet[25]. PD-L101 scored 30 by the SYFPEITHI algorithm and came out as the top candidate epitope.

In addition a 23 amino acid long from PD-L1 was synthesized (TAG Copenhagen, Copenhagen, Denmark): PDLong2:PDL1$_{242-264}$, VILGAILLCLGVALTFIFRLRKG (SEQ ID NO: 91). This long peptide contains a number of possible 15'mer HLA class II-restricted as well as minimal class I-restricted epitopes as predicted by the algorithm developed by Rammensee et al. available at world wide web syfpeithi.de[25]. Especially it contains the HLA-A2 epitope entitled PDL111 PDL1$_{250-58}$, CLGVALTFI—SEQ ID NO: 92). A 20-mer long peptide (here entitled 'irrelevant control') GARVERVDFGNFVFNISVLW—SEQ ID NO: 93—was used as control peptide as well as the HLA-A2 high affinity binding epitope HIV-1 pol$_{476-484}$ (ILKEPVHGV—SEQ ID NO: 94) was used as irrelevant controls.

Co-Stimulation Assays

PBMCs from malignant melanoma patients were stimulated with autologous DCvacc with ratio 1:10 DCvacc:PBMCs. A day after stimulation, cultures were divided and co-stimulated with peptides either with 25 µg/mL of PDLong1: PDL19-28, [FMTYWHLLNAFTVTVPKDL—SEQ ID NO: 89] or PDLong2: PDL1242-264, [VILGAILLCLGVALTFIFRLRKG—SEQ ID NO: 91] or irrelevant long peptide [GARVERVDFGNFVFNISVLW—SEQ ID NO: 93] as control co-stimulation. Second stimulation with DCvacc was performed on day 7 and followed by peptide co-stimulation on day 8. TL-2 (120 U/mL) was added a day after each peptide co-stimulations. A week after second peptide co-stimulation the cultures were analyzed for DCvacc response using intracellular cytokine staining.

Intracellular Cytokine Staining (ICS)

For detection of cell subpopulations producing cytokines (IFN-γ and TNF-α), PBMCs that were stimulated with DCvacc and co-stimulated with peptides for two weeks, were stimulated with DCvacc (ratio 1:10 DCvacc:PBMCs) for 5 hours at 37° C. with 5% $CO_2$. GolgiPlug (BD) was added at a dilution of 1:200 after the first hour of incubation. After 4 additional hours cells were washed twice with PBS, stained fluorochrome conjugated antibodies for surface markers (CD3-Amcyan, CD4-PerCP and CD8-Pacific Blue, all from BD). Cells were washed one additional time and thereafter were fixed and permeabilized with Fixation/Permeabilization and Permeabilization Buffer (eBioscience), according to manufacturer's instructions. Cells were subsequently stained with fluorochrome-conjugated antibodies for intracellular cytokines. The following combinations were used: IFN-γ-PE-CY7 (BD), TNF-α-APC (eBioscience). Relevant isotype controls were used to enable correct compensation and confirm antibody specificity. Stained cells were analyzed using a BD FACSCanto II flow cytometer and further analysis was performed with BD FacsDiva Software.

To determine PD-L1 response, cultures were stimulated with PDLong1 or PDLong2 (0.2 mmol/L) or an irrelevant peptide for 5 hr. Subsequently cells were stained surface and intracellular antibodies and further analysed on BD FACSCanto II.

ELISPOT

In the present study the ELISPOT was performed according to the guidelines provided by CIP (cimt.eu/cimt/files/dl/cip_guidelines.pdf). Briefly, nitrocellulose bottomed 96-well plates (MultiScreen MAIP N45; Millipore) were coated overnight with the relevant antibodies. The wells were washed, blocked by X-vivo medium and the cells were added if possible in triplicates otherwise in duplicates at different cell concentrations, with or without peptide. The plates were incubated four hours. Next, medium was discarded and the wells were washed prior to addition of the relevant biotinylated secondary Ab (Mabtech), followed by the Avidin-enzyme conjugate (AP-Avidin; Calbiochem/Invitrogen Life Technologies) and finally the enzyme substrate NBT/BCIP (Invitrogen Life Technologies). The spots were counted using the ImmunoSpot Series 2.0 Analyzer (CTL Analyzers).

CBA

To determine the changes in cytokine secretion in DCvacc stimulated and peptide co-stimulated (PDLong1 and PDLong2 or HIV peptide) cultures, cell culture supernatants were analyzed using BD™ Cytometric Bead Array (CBA) Flex Sets for IFN-γ, TGF-β1, TNF-α, IL-6, IL-10 and IL-17A. Flex sets for IFN-γ, TNF-α, IL-6 and IL-10 were combined, whereas IL-17A and TGF-β1 were analyzed separately. Analysis was performed according to the manufacturer's recommendations. Samples were acquired on FACSCANTO II (BD Biosciences) and data was analyzed using FCAP Array™ Software v 3.0.1 (BD Biosciences).

Results

Co-Stimulation with a Long PD-L1 Peptide Boosts T Cell Reactivity Against DCvacc In general, low immunity toward DCvacc was observed in the patients both before and after vaccination. In the present study, we set out to examine the supporting effects of PD-L1-specific T cells on the DCvacc-specific T cell response. Hence, PBMCs were isolated from patients with melanoma at baseline before vaccination as well as after four and, for some patients, after six vaccinations with DCvacc. PBMCs were stimulated twice with DCvacc in combination with either a control HIV epitope or PD-L1 peptides, as shown in FIG. 1A. Overall, we found that DCvacc mainly stimulates CD4$^+$ T cells. First we examined the effects of a previously described long T cell epitope from PD-L1 ("PDLong1" [PDL1$_9$-27, FMTYWHLLNAF-TVTVPKDL] SEQ ID NO: 89). [18] PDLong1 includes an HLA-A2-restricted, PD-L1-derived CD8$^+$ T cell epitope (PDL1$_{15-23}$, LLNAFTVTV—SEQ ID NO: 90). We observed an increase in the number of PBMCs that showed reactivity against DCvacc when they were cocultured with PDLong1 compared to the control HIV epitope. FIG. 1B to FIG. 1I show the results of cultures from three donors in which coactivation of PD-L1-specific T cells significantly boosted T cell immunity toward DCvacc. CD4$^+$ T cells released TNFα alone in response to DCvacc without co-stimulation (FIG. 1B and FIG. 1C). TNFα/INFγ double-positive CD4$^+$ T cells were induced by DCvacc with PD-L1 peptide co-stimulation (FIG. 1D and FIG. 1E). Reactive CD4+ and CD8$^+$ T cell numbers both increased in response to DCvacc with PD-L1 peptide co-stimulation (FIG. 1F to FIG. 1I).

In cultures of PBMCs before vaccination, co-stimulation with PDLong1 increased CD4$^+$ T cell reactivity toward DCvacc in six out of eight donors (P=0.312) and CD8$^+$ T cell reactivity in seven out of eight donors (P=0.039) (FIG.

Figure 2A:
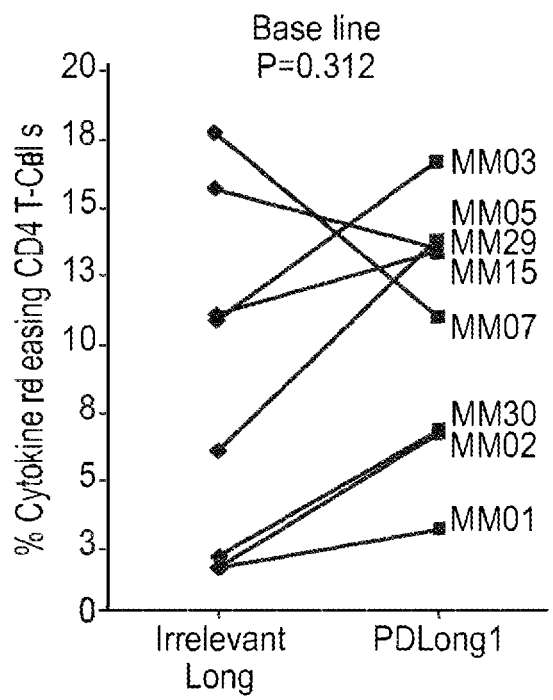
FIG. 2A-FIG. 2D. Costimulation of PBMCs with PDLong1 plus dendritic cell vaccine. At days 16-20, after two stimulations with DCvacc and two stimulations with either an irrelevant control peptide or PDLong1 peptide, the percentage of cells that released TNFα/INFγ in response to DCvacc was identified by flow cytometry. Percentages of DCvacc-reactive CD4$^+$ T cells in cultures of PBMCs taken from eight melanoma patients before vaccination (baseline.
Figure 2B:
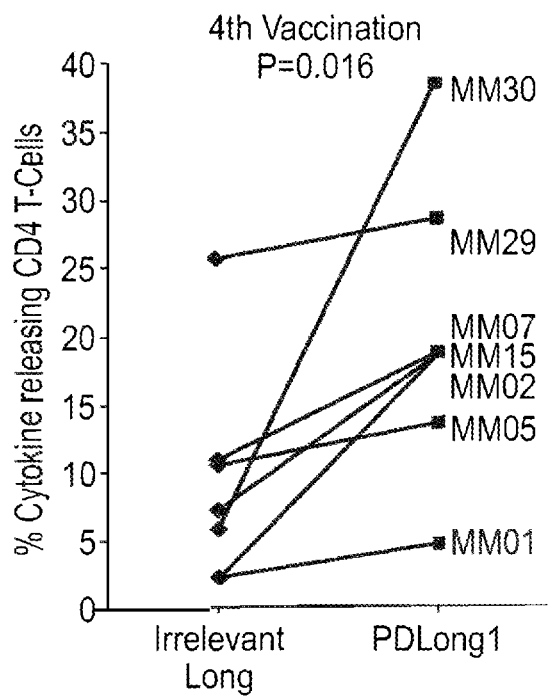
Figure 2C:
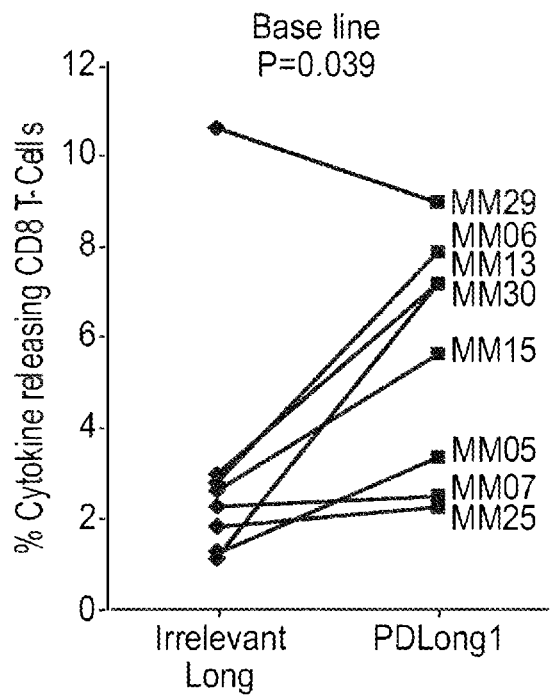
Figure 2D:
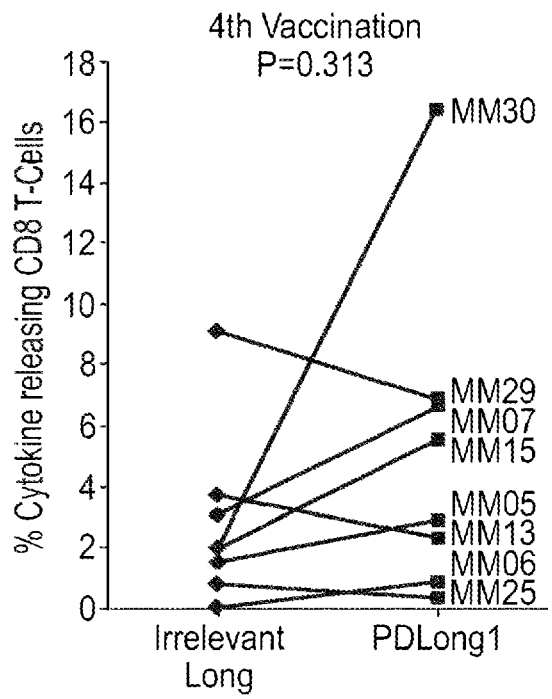

2A to FIG. 2D, respectively). After four vaccinations, CD4$^+$ T cell reactivity was increased in all donors (P=0.016) (FIG. 2A and FIG. 2B), whereas CD8$^+$ T cell reactivity was increased in only five out of eight donors (P=0.313) (FIG. 2C and FIG. 2D). Both CD4+ and CD8$^+$ T cells reacted to a significantly greater extent against DCvacc in cultures co-stimulated with PDLong1 peptide compared to cultures co-stimulated with control peptide (P=0.02 and P=0.05, respectively).

Spontaneous Immune Response Against a Novel Long PD-L1 Epitope

Figure 3A:
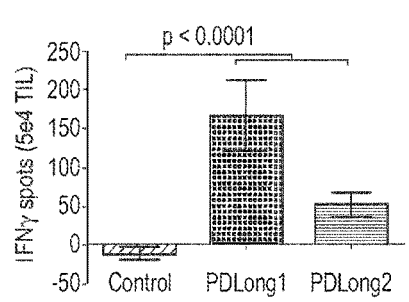
FIG. 3A-FIG. 3F. Natural T cell responses to PDLong1 and PDLong2.
Figure 3B:
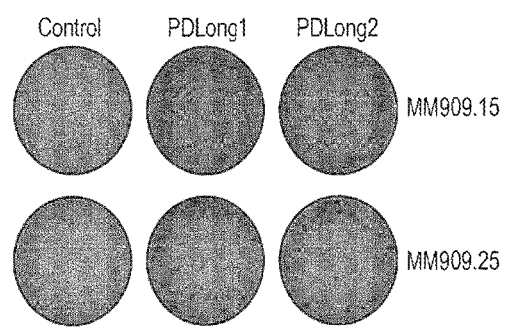
Figure 3C:
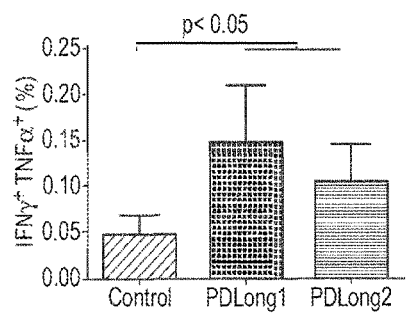
Figure 3D:
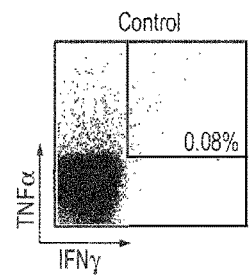
Figure 3E:
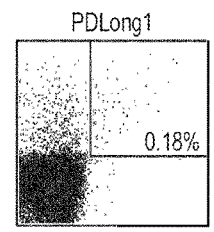
Figure 3F:
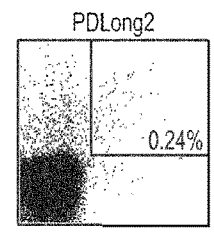

To further investigate whether the immune response against PD-L1 could be augmented by co-stimulation, we used the IFNγ ELISPOT assay to examine tumor-infiltrating lymphocytes from 12 melanoma patients for T cell reactivity against an additional PD-L1 derived epitope (PDLong2 [PDL1$_{242-264}$, VILGAILLCLGVALTFIFRLRKG (SEQ ID NO: 91)]). The IFNγ ELISPOT assay revealed an increased T cell response in tumor-infiltrating lymphocytes cultured with PDLong2 (FIG. 3A and FIG. 3B). This increased response was confirmed by intracellular cytokine staining (FIG. 3C to FIG. 3F).

Co-stimulation with two long PD-L1 peptides boosts T cell reactivity against DCvacc Next, we examined PBMCs from eight vaccinated melanoma patients to determine the effects of co-stimulation with both PDLong1 and PDLong2 (FIG. 4A to FIG. 4D). We observed a significant increase in the number of CD4$^+$ T cells that reacted against DCvacc in cultures that had been co-stimulated with both PDLong epitopes compared to those co-stimulated with the control peptide (P=0.008 at baseline and P=0.008 after the fourth vaccination). Hence, CD4$^+$ T cell reactivity was increased in all donors at both time points. CD8$^+$ T cell reactivity was likewise significantly increased at baseline (P=0.008) and after the fourth vaccination (P=0.055) in all but one donor.

Mann-Whitney tests revealed that PD-L1 co-stimulation had a significant effect on T cell response when we compared all cultures stimulated with either one or two PD-L1 epitopes to cultures incubated with control peptide. CD4$^+$ T cell response: P=0.012 at base line, P=0.002 after fourth vaccination, and P=0.095 after sixth vaccination. CD8$^+$ T cell response: P=0.01 at baseline, P=0.076 after fourth vaccination, and P=0.31 after sixth vaccination.

Co-Stimulation with PD-L1 Epitopes Induces IL-6 Production

Figure 5A:
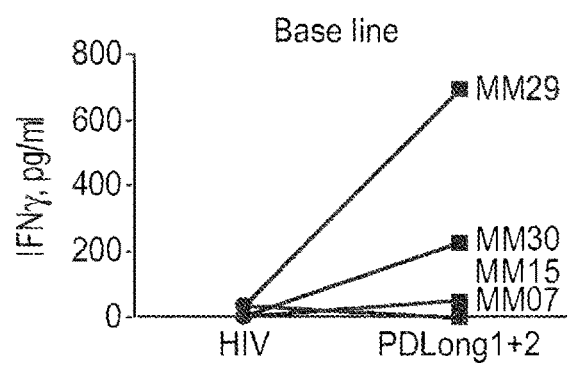
FIG. 5A-FIG. 5H. Comparison of cytokine secretion in supernatants from cultures of cells from four patients. Supernatants from cultures either costimulated with an irrelevant control peptide or with PDLong1 plus PDLong2 were collected on the day of analysis of DCvacc-reactive T cells so that (1) the presence of IFNγ could be measured before vaccination (baseline.
Figure 5B:
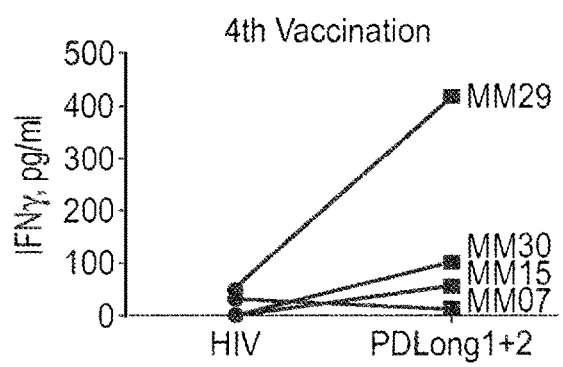
Figure 5C:
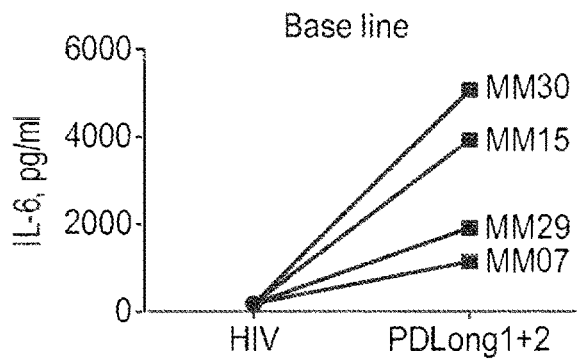
Figure 5D:
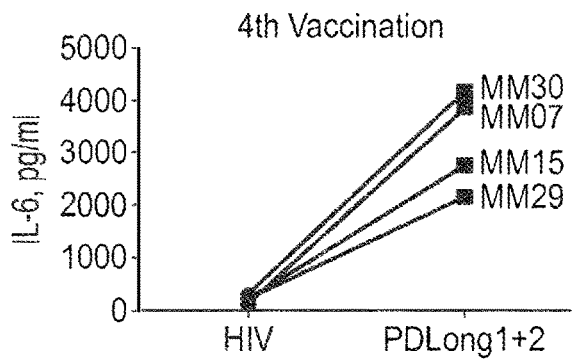
Figure 5E:
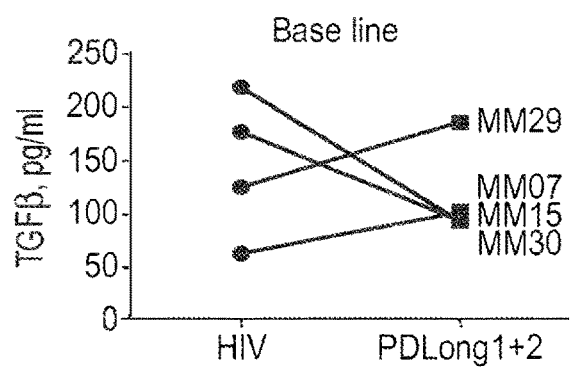
Figure 5F:
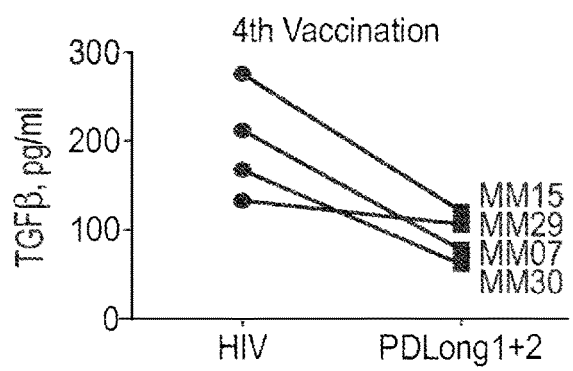
Figure 5G:
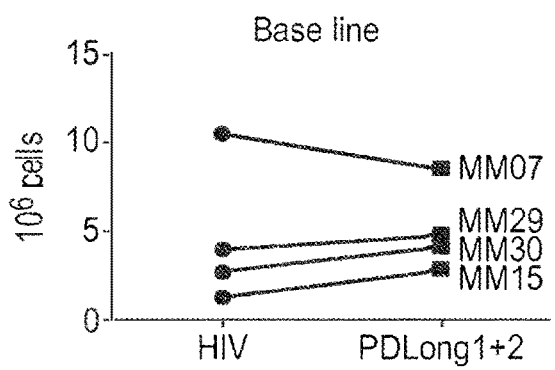
Figure 5H:
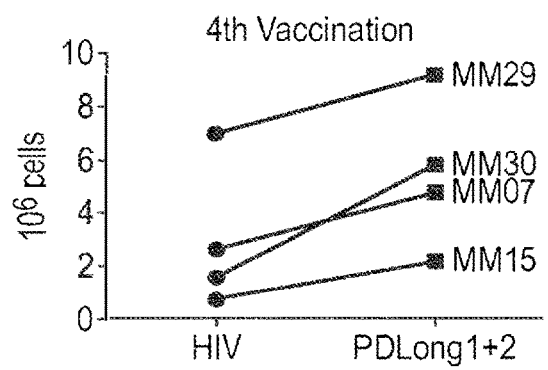

To examine changes in the cytokine regulatory environment, we used BD™ Cytometric Bead Array (CBA) Flex Set assays to compare cytokine secretion in the supernatants of cultures of PBMCs from four donors. PBMC cultures co-stimulated with the PDLong epitopes showed higher concentrations of proinflammatory cytokines INFγ and IL6 compared to control cultures. Higher IFNγ levels compared to control cultures were observed in cultures from three out of four patients at baseline and after the fourth vaccination (FIG. 5A and FIG. 5B). In addition, a large increase in IL-6 levels was observed in all four patients after co-stimulation with both PDLong peptides (Long 1+2) compared to incubation with control peptide at both time points (FIG. 5C and FIG. 5D). We also observed lower levels of the regulatory cytokine TGFβ in cultures co-stimulated with both PDLong peptides compared to controls (FIG. 5E and FIG. 5F). These lower levels of TGFβ were seen in PBMC cultures from two out of four patients at baseline and all four patients after the fourth vaccination/co-stimulation. Other cytokines were measured, such as TNFα, IL10, and IL17, but they could not be detected in any of the supernatants examined (data not shown). In addition to changes in the cytokine profile, cell numbers were higher in most cultures co-stimulated with the PD-L1 epitopes compared to control cultures (FIG. 5G and FIG. 5H). The increased numbers of cells were observed in cultures from three out of four patients at baseline and from all four patients after the fourth stimulation.

Discussion

Several potential therapeutic strategies that target immunosuppression in cancer are currently under investigation, such as the blocking of inhibitory pathways with monoclonal antibodies. [19] An alternative strategy, which we have adopted, is to utilize specific T cells to target immune suppression. [20] In the present study, when we examined the effect on immunogenicity of co-stimulating a DC-based vaccine with long peptide epitopes derived from PD-L1, we found that T cell reactivity toward the vaccine was significantly increased. Reactivity of CD4$^+$ T cells increased the most, but CD8$^+$ T cell reactivity was also significantly boosted by co-stimulation.

In general, we only observed no or very limited reactivity towards DCvacc in PBMC from patients ex vivo (Borch et al., in preparation). Hence, there was only limited induction of T cell frequencies in vivo in patients vaccinated with DCvacc. This may have been due to the presence of different immunosuppressive mechanisms that may even be boosted by the DCs. Regulatory feedback mechanisms, such as upregulation of PD-L1, are essential in order to limit the intensity and extent of immune responses, which might otherwise cause harm to the host. However, this immune evasion is detrimental within the context of cancer immunotherapy. Thus, the targeting of one or more immunosuppressive pathways may be useful in combination with anti-cancer immunotherapy in cases where immunosuppressive mechanisms may suppress the effects of therapy.

The results of the present study suggest that the addition of PD-L1 epitopes to a cancer vaccine could strengthen immune responses against the vaccine in vivo. These measures may boost effector T cells by coactivation of proinflammatory PD-L1-specific T cells, which are attracted to the tumor microenvironment due to local expression of PD-L1. Previous studies have reported that exposure of regulatory T cells (Tregs) to IL-6 and other proinflammatory cytokines induces reprogramming of mature Tregs to acquire a phenotype resembling proinflammatory Th17 cells. [21-23] In the present study, IL-6 levels were significantly higher in cultures that had been co-stimulated with PD-L1 epitopes. Hence, PD-L1-specific T cells may effectively boost the effector phase of the immune response by both direct and indirect release of proinflammatory cytokines, as well as by direct removal of PD-L1-expressing regulatory immune cells that inhibit PD-1-positive T cells. In addition to directly restraining the immune-regulatory effects of PD-L1, PD-L1-specific T cells may inhibit other routes of immune suppression mediated by their cognate target cells.

Early successes in blocking the PD-1 pathway have resulted in commercial interest and competition among drug companies to develop monoclonal antibodies targeting PD-1 or PD-L1. Combined PD-1 pathway blockade with vaccination is a promising alternative approach, as vaccines have been shown to recruit immune effector cells into the tumor microenvironment. Targeting immune regulation by induction of PD-L1-specific T cells is an attractive option to boost the immunogenicity of immunotherapeutic agents, as boosting PD-L1-specific T cells may directly modulate immune regulation and alter tolerance. The combination of vaccination with PD-1 pathway blockade should be easily implementable and synergistic, since PD-L1 blockade by antibodies would make the PD-L1-expressing target cells more vulnerable targets for vaccine-induced T cells. Future investigations are required to confirm the safety, tolerability, and effectiveness of a regimen that includes co-stimulation of PD-L1-specific T cells with PD-L1-derived epitopes.

Example 2

Spontaneous Immune Responses Against 10104.1 in Human Patients

We first analysed the immune responses against two versions of 10104.1 in Tumor infiltrating T cells from melanoma patients. Next we analysed if PDL111 specific T cells were able to recognize IO104.1

Materials and Methods

Peptides

```
PDL111 =
CLGVALTFI (minimal epitope - SEQ ID NO: 92)

IO104 (PDLong2) =
VILGAILLCLGVALTFIFRLRKG (SEQ ID NO: 92)

IO104.1-OH =
Arg-Thr-His-Leu-Val-Ile-Leu-Gly-Ala-Ile-Leu-

Leu-Cys-Leu-Gly-Val-Ala-Leu-Thr-Phe-Ile-Phe-

Arg-Leu-Arg-Lys-Gly-Arg-OH
(C-terminus acid) (SEQ ID NO: 52)

IO104.1-NH₂ =
Arg-Thr-His-Leu-Val-Ile-Leu-Gly-Ala-Ile-Leu-

Leu-Cys-Leu-Gly-Val-Ala-Leu-Thr-Phe-Ile-Phe-

Arg-Leu-Arg-Lys-Gly-Arg-NH2
(C-terminus amide) (SEQ ID NO: 52 with C
terminal amide)
```

ELISPOT Assay

The ELISPOT technique enabled screening a high number of peptide antigens for T-cell recognition, despite the availability of relatively few T-cells. We used the ELISPOT assay to quantify peptide-specific, effector cells that secreted IFN-γ, as described in Example 1. We performed the assays according to the guidelines provided by the cancer immunotherapy immunoguiding program (CIP; cimt.eu/cimt/files/dl/cip_guidelines.pdf). To measure T-cell reactivity, nitrocellulose-bottomed 96-well plates (MultiScreen MSIPN4W; Millipore) were coated overnight with the relevant antibodies. The wells were washed and blocked with X-vivo medium for 2 h. The Tumor Infiltrating Lymphoctyes (TILs) were added at different cell concentrations in triplicate wells, with PD-L1 peptides or with control peptide, and incubated overnight. The following day, the wells were washed, and the relevant biotinylated secondary antibody (Mabtech) was added, followed by the avidin-enzyme conjugate (AP-Avidin; Calbiochem/Invitrogen Life Technologies); finally, we added the enzyme substrate, NBT/BCIP (Invitrogen Life Technologies) for visualization. The spots on the developed ELISPOT plates were analyzed on a CTL ImmunoSpot S6 Ultimate-V analyzer with Immunospot software, v5.1.

Results

Figure 6:
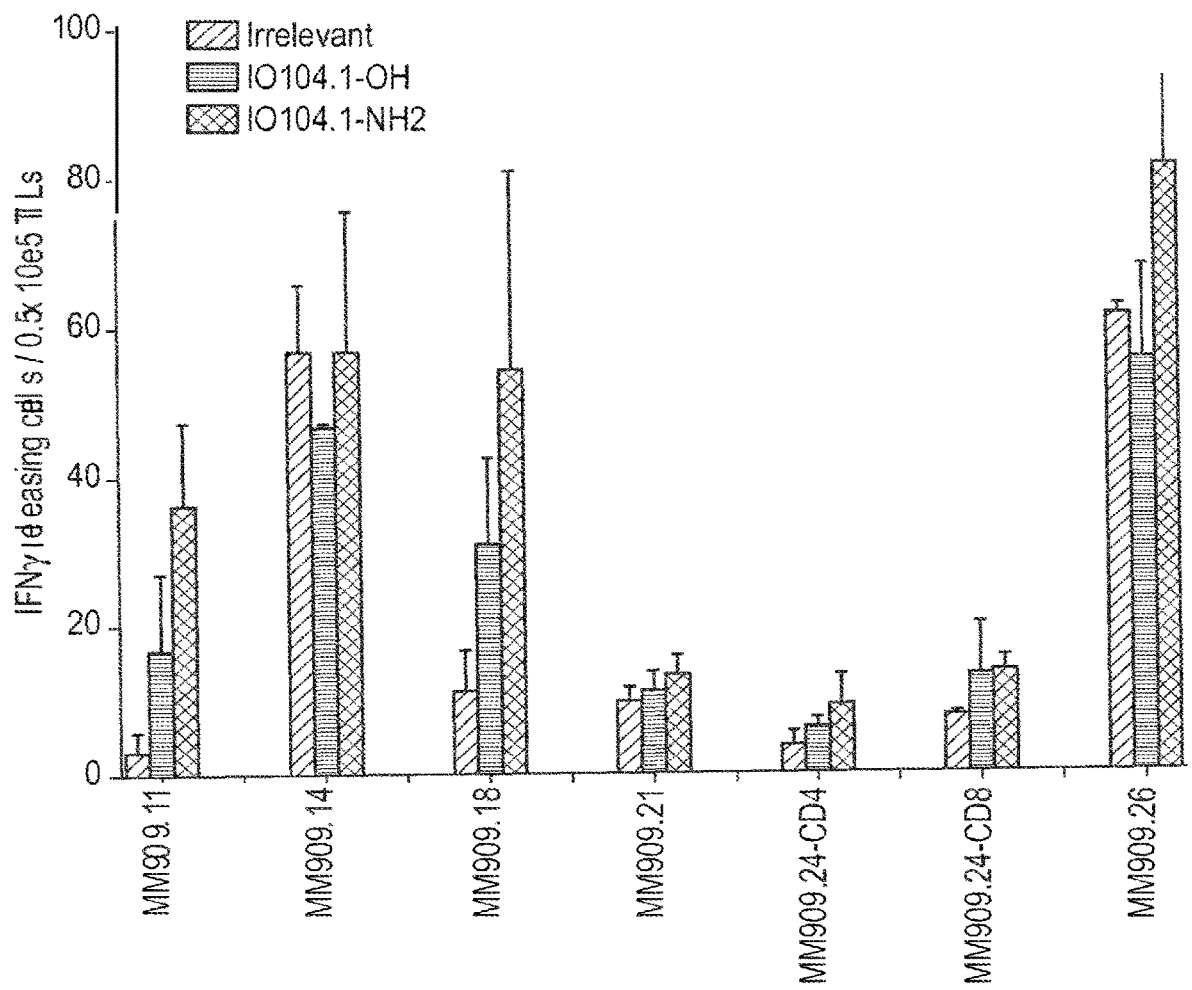
FIG. 6. Measurement of IFN γ releasing cells in tumor infiltrating lymphocytes of melanoma patients in response to 10104.1-OH and 10104.1-NH$_2$ versus an irrelevant control peptide.

We used the IFNγ ELISPOT assay to examine tumor-infiltrating lymphocytes from 7 melanoma patients for T cell reactivity against IO104.1 peptides. The IFNγ ELISPOT assay revealed a T cell response in tumor-infiltrating lymphocytes cultured with IO104.1 peptides from three of the patients. See FIG. 6.

Figure 7:
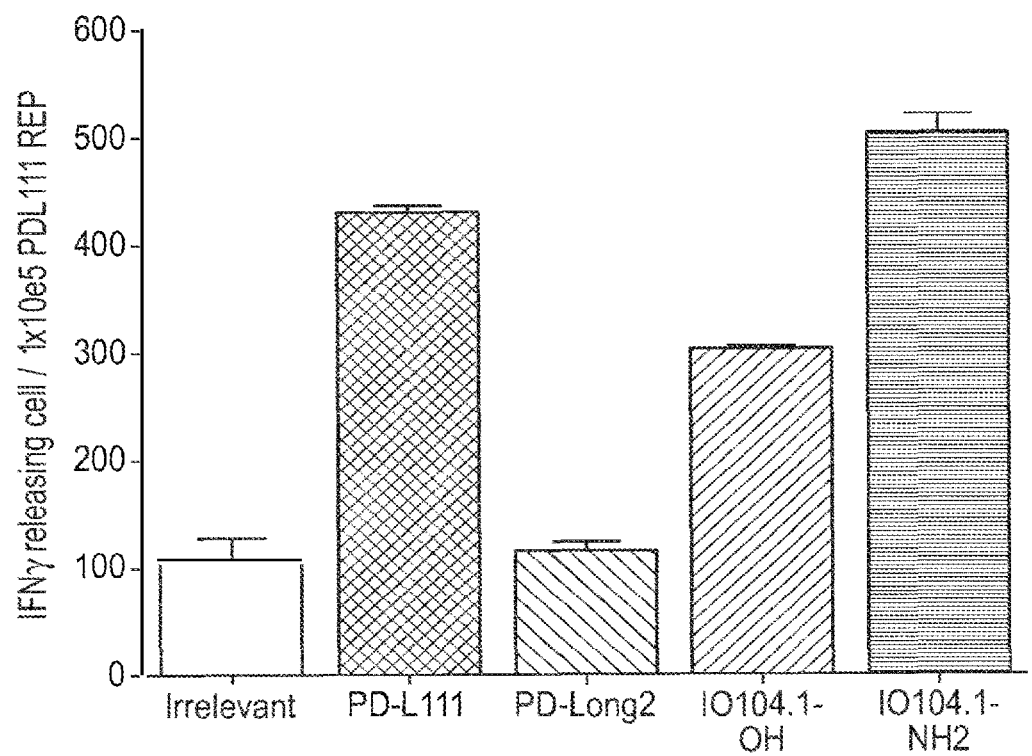
FIG. 7. ELISPOT comparison of PDL111-specific CD8-T cell responses to PDLong2, 10104.1-OH, 10104.1-NH$_2$. PDL111 and an irrelevant control peptide.
Figure 8A:
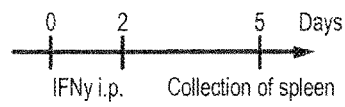
FIG. 8A-FIG. 8D. T cells specific for murine PDL1 are naturally occurring in mice.
Figure 8C:
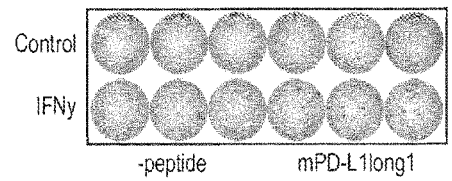
Figure 8B:
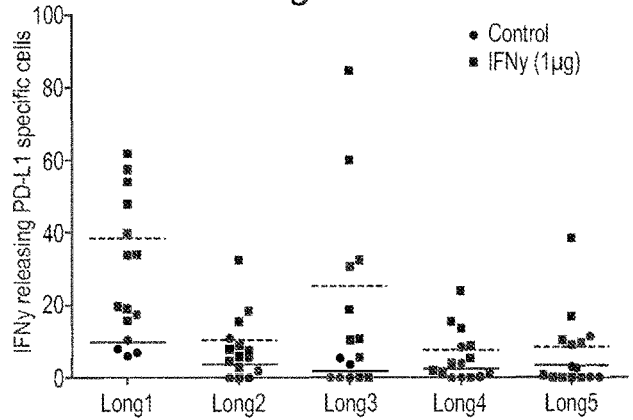
Figure 8D:
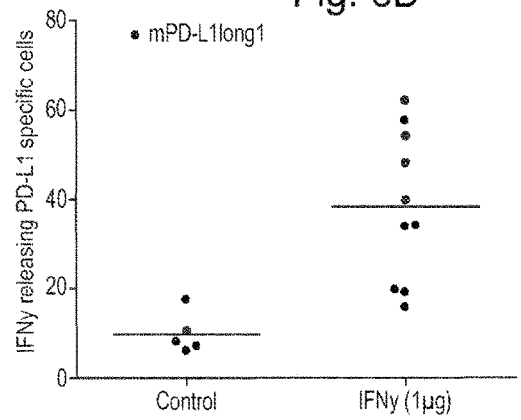
Figure 9A:
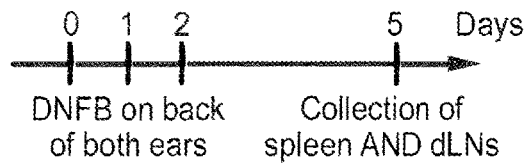
FIG. 9A-FIG. 9D. Local inflammation caused by the allergen 2,4-dinitrofluorobenzene (DNFB) elicits a PD-L1-specific T cell response in mice.
Figure 9B:
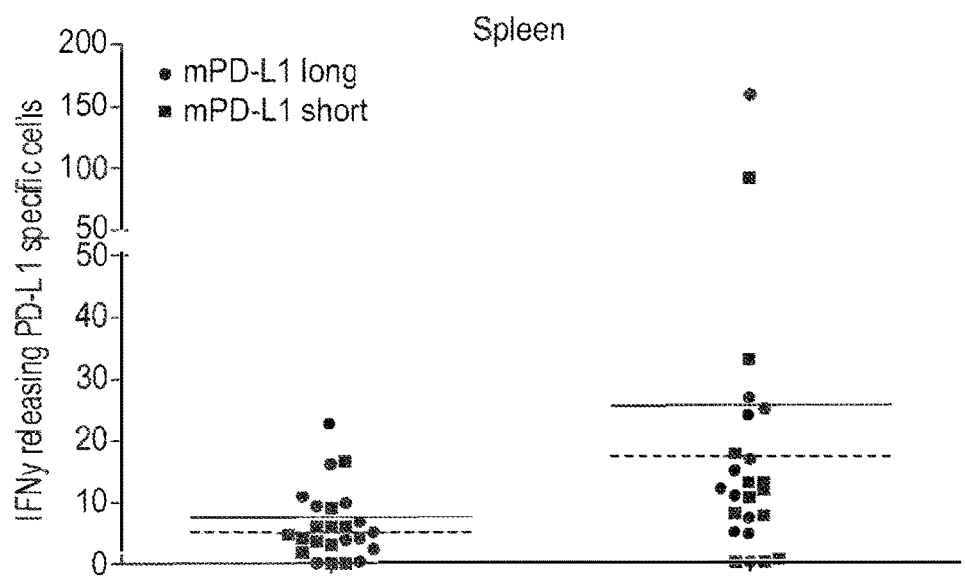
Figure 9C:
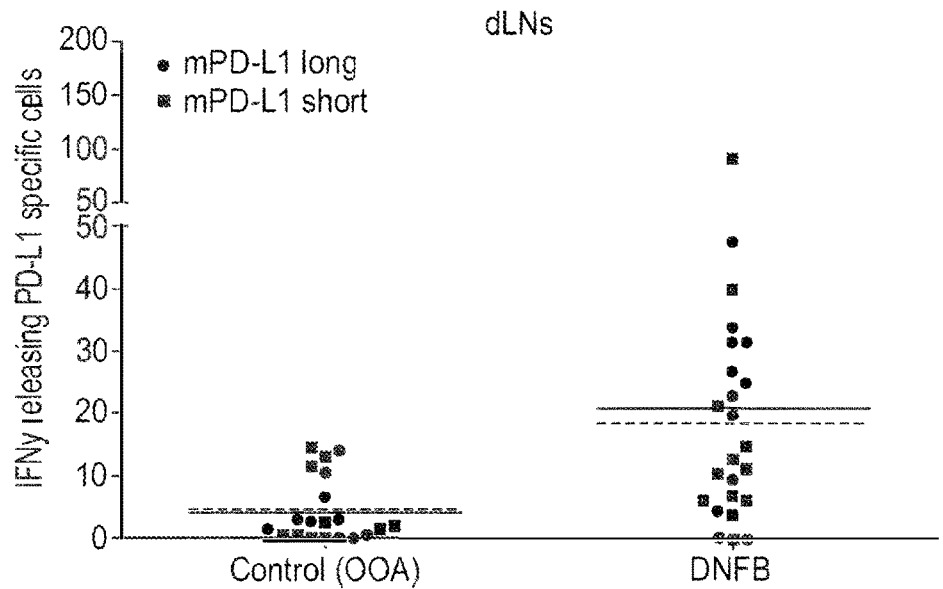
Figure 9D:
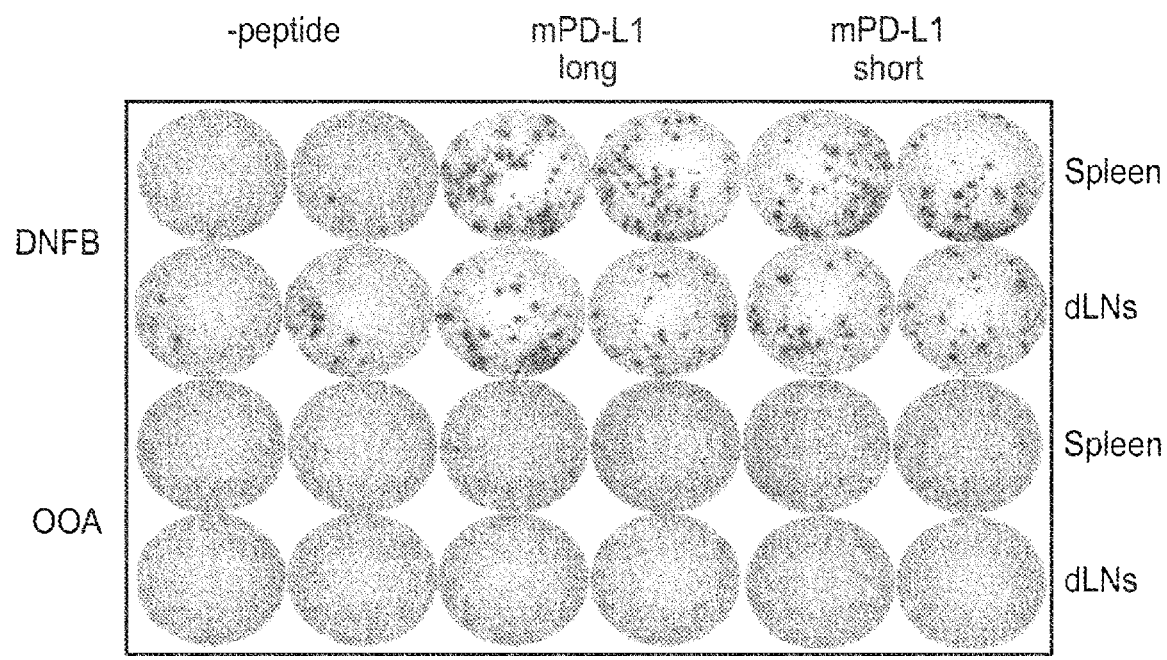

Next, we examined if CD8 T-cells specific for the minimal epitope C L G V A L T F I (PDL111—SEQ ID NO: 92, which is located within IO104.1) were able to recognize both versions of 10104.1 by ELISPOT. We analysed the reactivity towards PDL111, $PDL1_{242-264}$ (VIL-GAILLCLGVALTFIFRLRKG— PDLong2, SEQ ID NO: 91), 10104.1 (—OH) and 10104.1 (NH). The T cells were able to react toward both versions of IO104.1. See FIG. 7.

CONCLUSION

IO104.1 specific T cells are naturally present among tumor infiltrating lymphocytes (TILs) of human melanoma patients. 10104.1 peptides are also recognized by $CD8^+$ T cells specific for a known epitope of PD-L1 which is comprised within the sequence of 10104.1.

Example 3—PDL1 Specific T Cells are Naturally Occurring in Mice

We hypothesized that if PD-L1 specific T cells are natural occurring, they should activate and expand in response to inflammation.

Materials and Methods

C56BL/6 mice were injected with 1 μg IFNγ in 200 μl PBS i.p (or no injection for control) two days apart (day 0+2) to simulate inflammation. On day 5 the mice were sacrificed and a single cell solution of the removed spleen was made for further analysis by IFNγ-Elispot.

$9 \times 10^5$ splenocytes/well were stimulated ex vivo in Elispot plates with 5 μg/ml peptides from murine (m)PDL1 for 18-20 hours. Spot count for the peptide stimulated wells was subtracted the background (spot count of wells with no peptide stimulation).

The peptides from PDL1 were selected based on the following reasoning. The sequence of mPD-L1 is:

MRIFAGIIFT ACCHLLRAFT ITAPKDLYVV EYGSNVTME

CRFPVERELD LLALVVYWE KEDEQVIQFV AGEEDLKPQH

SNFRGRASLP KDQLLKGNA ALQITDVKLQ DAGVYCCII

SYGGADYKRI TLKVNAPYRK INQRISVDPA TSEHELICQ

AEGYPEAEVI WTNSDHQPV SGKRSVTTSR TEGMLLNVTS

SLRVNATAND VFYCTFWRS QPGQNHTAEL IIPELPATH

-continued

PPQNRTHWVL LGSILLFLIV VSTVLLFLRK QVRMLDVEK

CGVEDTSSKN RNDTQFEET
(SEQ ID NO: 95 - N-terminal/signal sequence
in bold, C-terminal/membrane-spanning region
underlined)

This sequence is significantly different to that of human (h)PDL1, so it is not possible to use the same peptides for testing in mice as in humans. However, we deliberately selected peptides from the regions of mPDL1 which correspond approximately to those regions in hPDL1 from which the sequences of PDlong1 and PDlong2 are derived (see Examples 1 and 2). That is, from the N terminal/signal sequence and the C terminal/membrane-spanning region of mPDL1.

The following peptides were chosen:

```
                                    (mLong1; SEQ ID NO: 96)
            MRIFAGIIFTACCHLLRA (mLong2; SEQ ID NO: 97)
            FTACCHLLRAFTITAPKDL (mLong3; SEQ ID NO: 98)
            WVLLGSILLFLIVVSTVLLFLRKQV (mLong4; SEQ ID NO: 99)
            TVLLFLRKQVRMLDVEKCGV (mLong5; SEQ ID NO: 100)
            MLDVEKCGVEDTSSKNRNDTQFEET
``` mLong1 and 2 are overlapping sequences from the region of mPDL1 shown in bold above; mLong3, 4 and 5 are overlapping sequences from the region of mPDL1 shown under-lined above. mLong1 is considered to be the closest mouse equivalent to the human peptide of PDlong1. mLong3 is considered to be the closest mouse equivalent to the human peptide of PDlong2.

Results and Conclusion

Result of the Elispot are shown in FIG. 8A to FIG. 8D. All 5 murine peptides were recognized by T cells following the prior stimulation with INFγ, thus indicating that T cells specific for epitopes within these sequences are naturally present in mice even without vaccination. The most positive results were obtained with mLong1 and mLong3. In subsequent murine experiments, for simplicity only mLong1 was used, but similar results would be expected with at least mLong3.

Example 4—Further Support for Naturally-Occurring PDL1 Specific T Cells in Mice

Given the result in Example 3, we hypothesized PD-L1 specific T cells should also activate and expand in response to local stimulation, such as the inflammatory response to an allergen.

Materials and Methods

A solution of 0.15% 2,4-dinitrofluorobenzene (DNFB; an allergen) in 1:4 olive oil/ace-tone (OOA) (or just OOA as a control) was painted on back of both ears of C56BL/6 mice for 3 consecutive days (days 0-2). On day 5 the mice were sacrificed and a single cell solution of the removed spleen and draining lymph nodes (dLNs) was made for further analysis by IFNγ-Elispot.

$8-9 \times 10^5$ cells/well were stimulated ex vivo in Elispot plates with 5 μg/ml mPD-L1long1 (mLong1 from Example 3) or mPD-L1short (a part of the mLong1 peptide having the sequence GIIFTACCHL (SEQ ID NO: 101)) for 18-20 hours. Spot count for the peptide stimulated wells was subtracted the background (spot count of wells with no peptide stimulation).

Results and Conclusion

Results of the Elispot are shown in FIG. 9A to FIG. 9D. Splenocytes and dLNs recognized both the long and short peptides in mice treated with DNFB, but not with control, confirming that naturally-occurring PDL1 specific T cells do indeed activate and expand in response to local allergen stimulation. The responses to both long and short peptides shows that the response is likely due to both CD8+ and CD4+ T cells. The short peptide should only be bound and presented by MHC class I and hence can only stimulate CD8+ T cells. The long peptide will (after processing) potentially be bound and presented by MHC class I and II, hence stimulating both CD8+ and CD4+ T cells.

Example 5—PDL1-Specific Responses in Mice are Increased by Vaccination with PDL1 Peptides Materials and Methods C56BL/6 mice were vaccinated subcutaneously (s.c) on the lower back with 100 μg mPD-L1long1 (mLong1 from Example 3) with or without Montanide as an adjuvant (only Montanide as a control) at day 0. On day 7 the mice were sacrificed and a single cell solution of the removed spleen was made for further analysis by IFNγ-Elispot.

$9 \times 10^5$ splenocytes/well were stimulated ex vivo in Elispot plates with 5 μg/ml mPD-L1long1 or mPD-L1short for 18-20 hours. Spot count for the peptide stimulated wells was subtracted the background (spot count of wells with no peptide stimulation).

Results and Conclusion

Figure 10A:
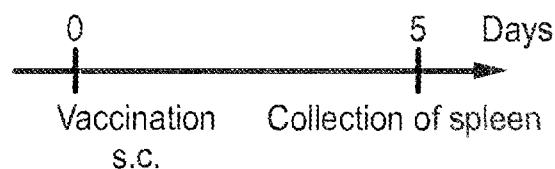
FIG. 10A shows the timeline for the experiment described in Example 5.
Figure 10B:
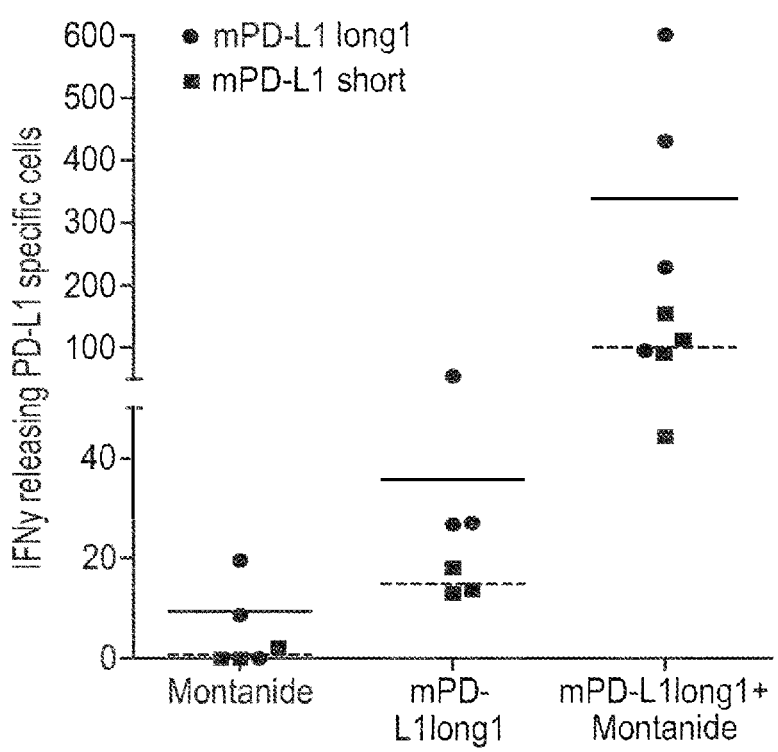
(FIG. 10B) Elispot results for splenocytes stimulated with mPD-L1long1 or mPD-L1 short ex vivo.
Figure 10C:
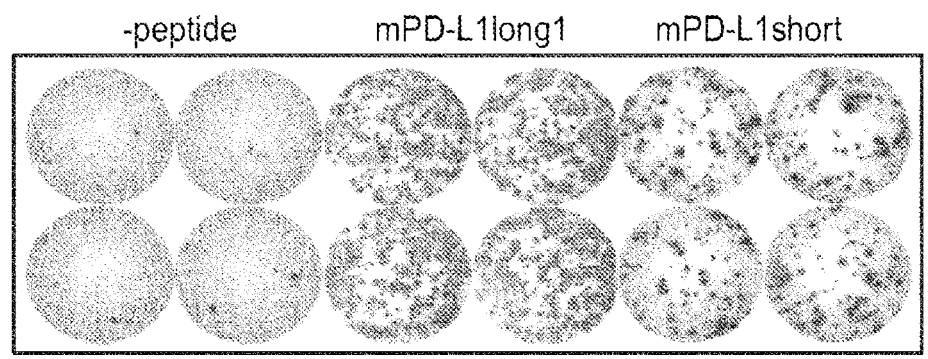
(FIG. 10C) Elispot wells of a representative mouse from each group. n=3-4 mice/group.
Figure 11A:
FIG. 11A-FIG. 11D. Vaccination with mPD-L1long1 shows antitumor effect in mice.
Figure 11B:
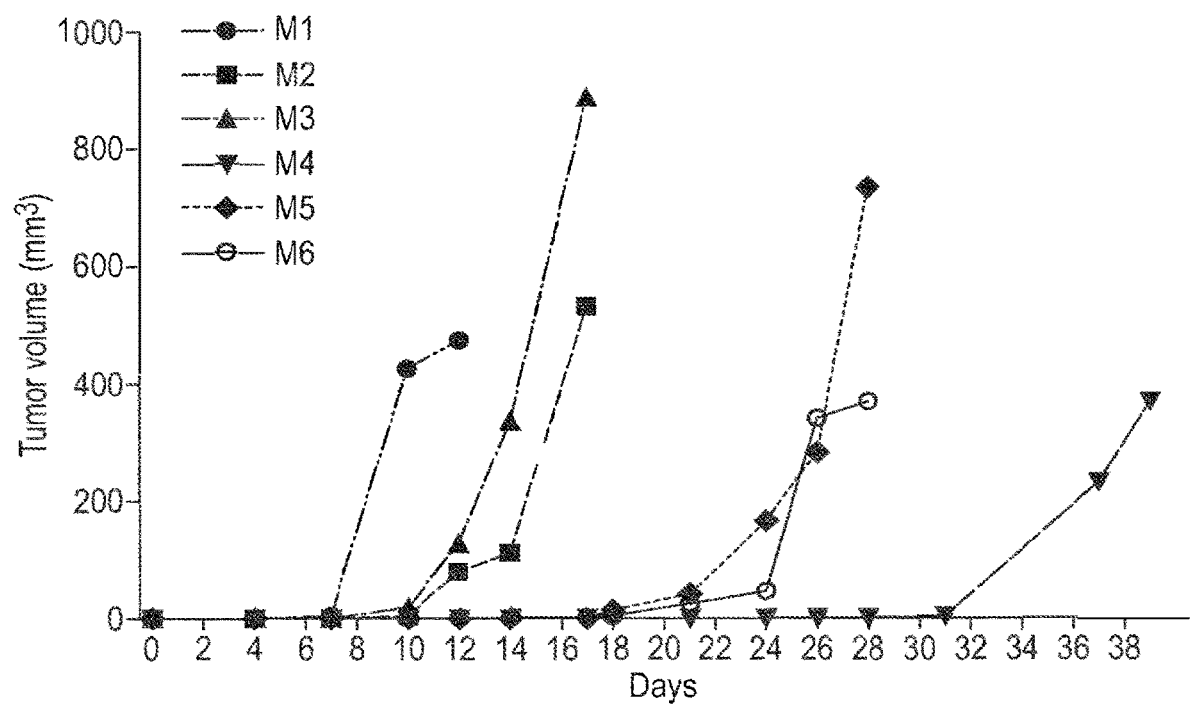
Figure 11C:
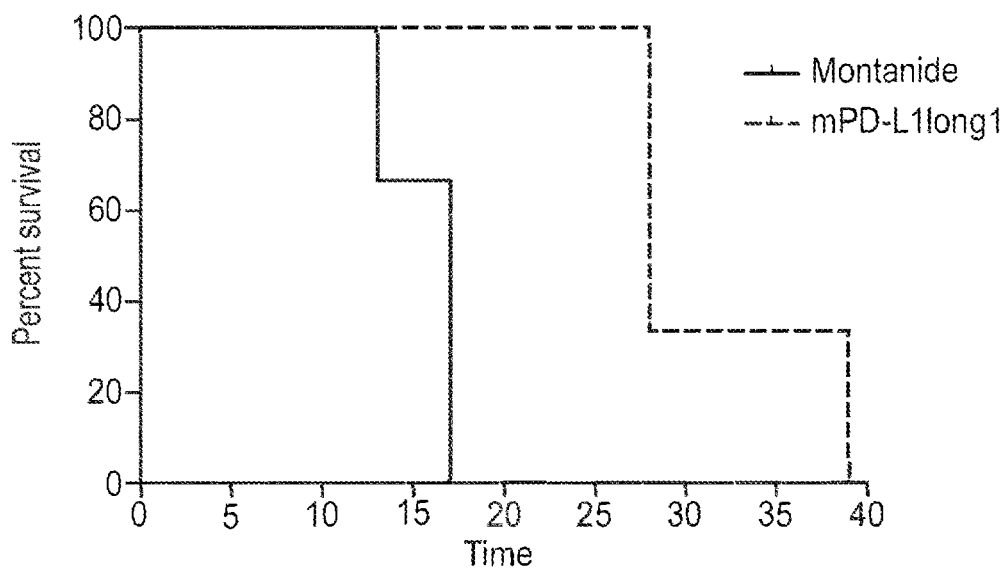
Figure 11D:
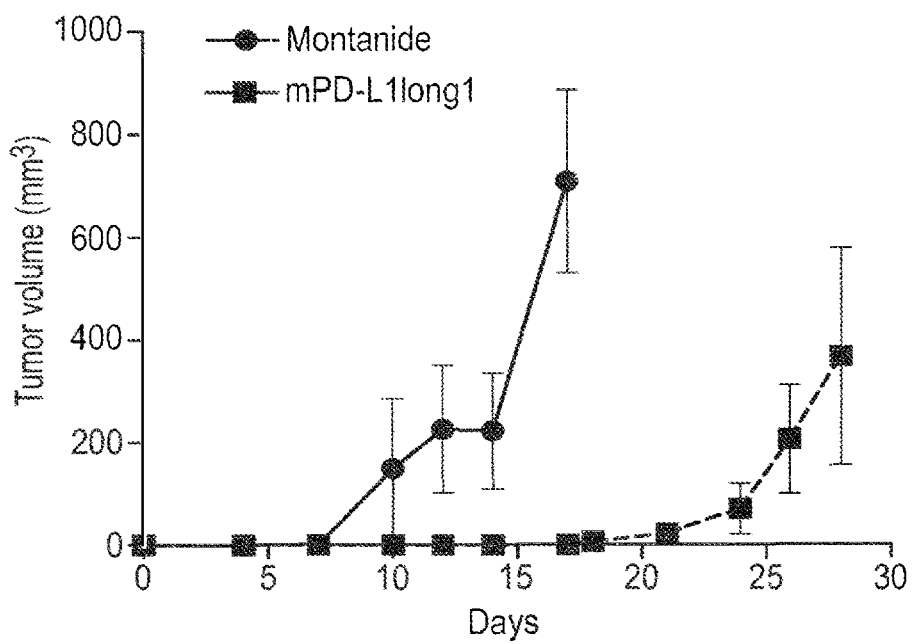

Results of the Elispot are shown in FIG. 10A to FIG. 10C. A strong PD-L1-specific T cell response was seen in the spleens and draining lymph nodes (DLNs) of the peptide-vaccinated mice compared to mice vaccinated with the adjuvant alone. Ex vivo stimulation with both mPD-L1long and the shorter version mPD-L1 short showed increased PD-L1-specific response in mPD-L1long vaccinated mice seen by IFNγ Elispot.

Example 6—Vaccination with mPD-L1long1 Shows Anti-Tumor Effect in Mice

Materials and Methods

C56BL/6 mice were inoculated with $2 \times 10^5$ B16F10 tumor cells subcutaneously (s.c) on one side of lower back (day 0). The tumor cells were pre-stimulated with IFNγ in vitro for 24 h before inoculation. At day 0 and day 7 mice were vaccinated s.c on the other side of lower back with 100 μg mPD-L1long1 with Montanide as an adjuvant (only Montanide as a control). Tumor size was measured 3×/week and mice were sacrificed when tumors got too big.

Results and Conclusion

Results are shown in FIG. 11A to FIG. 11D. The mice vaccinated with peptide+montanide showed reduced tumor growth and better survival than mice vaccinated with montanide only. Thus anti-PDL1 T cells expanded and activated by the vaccination have an antitumoral effect.

Overall Conclusion for Examples 3 to 7 (In Vivo Testing)

We describe that PD-L1 specific T cells are expanded by IFNγ injections (Example 3) and local stimulation with allergens (Example 4), which suggests that PD-L1 specific T cells are already present and are activated and proliferate upon receipt of a strong activation signal from their cognate targets (i.e. professional antigen-presenting cells) at inflammation sites. We demonstrate that PD-L1 specific T cells are easily expanded by vaccination and that an antitumoral effect results. Thus, PD-L1-specific T cells are a particularly interesting example of the immune system's ability to influence adaptive immune responses by directly reacting against the immune-suppressive mechanisms employed by cancerous cells. Vaccination using PDL1 peptides has been shown to have a direct benefit in vivo.

General Details for Elispot Methodology

Following sacrifice of mice, spleen (and draining lymph nodes (dLNs)) were removed.
Spleen and dLNs was smashed through a 70 μM cell strainer into a 50 ml tube with media (RPMI+10% FCS+1% pen/strep) and washed for at 300 G for 5 minutes, repeated for dLNs. Splenocytes was lysed with RBC lysis buffer for 1 min and washed in media twice.
Cells were counted and transferred to IFNγ Ab-coated Elispot plates in cell number of 9×10⁵ cells/well. Coating antibody: Anti-mouse IFN-g mAb AN18 (Mabtech cat no. 3321-3-1000).
Stimulatory peptides were added to designated wells in concentrations of 5 μg/ml. Control wells were not stimulated with peptide.
Elispot plates were developed after 18-20 hours.
Detection antibody Anti-mouse IFN-g mAb R4-6A2-Biotin (Mabtech cat no. 3321-6-1000). Avidin-enzyme conjugate (AP-Avidin; Calbiochem/Invitrogen Life Technologies) and enzyme substrate, NBT/BCIP (Invitrogen Life Technologies) used for visualization.
Spot count for peptide-stimulated wells was always subtracted the corresponding wells without peptide stimulation (the background)
Negative values were sat to zero.

Full Length Sequence of Human PD-L1 (SEQ ID NO. 1)

```
Met Arg Ile Phe Ala Val Phe Ile Phe Met Thr Tyr
1               5                   10
Trp His Leu Leu Asn Ala Phe Thr Val Thr Val Pro
            15                  20
Lys Asp Leu Tyr Val Val Glu Tyr Gly Ser Asn Met
25                  30                      35
Thr Ile Glu Cys Lys Phe Pro Val Gly Lys Gln Leu
                40                  45
Asp Leu Ala Ala Leu Ile Val Tyr Trp Glu Met Glu
50                  55                      60
```

-continued

```
Asp Lys Asn Ile Ile Gln Phe Val His Gly Glu Glu
                65                  70
Asp Leu Lys Val Gln His Ser Ser Tyr Arg Gln Arg
            75                  80
Ala Arg Leu Leu Lys Asp Gln Leu Ser Leu Gly Asn
85                  90                      95
Ala Ala Leu Gln Ile Thr Asp Val Lys Leu Gln Asp
                100                 105
Ala Gly Val Tyr Arg Cys Met Ile Ser Tyr Gly Gly
        110                 115                 120
Ala Asp Tyr Lys Arg Ile Thr Val Lys Val Asn Ala
                125                 130
Pro Tyr Asn Lys Ile Asn Gln Arg Ile Leu Val Val
            135                 140
Asp Pro Val Thr Ser Glu His Glu Leu Thr Cys Gln
145                 150                 155
Ala Glu Gly Tyr Pro Lys Ala Glu Val Ile Trp Thr
                160                 165
Ser Ser Asp His Gln Val Leu Ser Gly Lys Thr Thr
    170                 175                 180
Thr Thr Asn Ser Lys Arg Glu Glu Lys Leu Phe Asn
                185                 190
Val Thr Ser Thr Leu Arg Ile Asn Thr Thr Thr Asn
            195                 200
Glu Ile Phe Tyr Cys Thr Phe Arg Arg Leu Asp Pro
205                 210                 215
Glu Glu Asn His Thr Ala Glu Leu Val Ile Pro Glu
                220                 225
Leu Pro Leu Ala His Pro Pro Asn Glu Arg Thr His
    230                 235                 240
Leu Val Ile Leu Gly Ala Ile Leu Leu Cys Leu Gly
                245                 250
Val Ala Leu Thr Phe Ile Phe Arg Leu Arg Lys Gly
            255                 260
Arg Met Met Asp Val Lys Lys Cys Gly Ile Gln Asp
265                 270                 275
Thr Asn Ser Lys Lys Gln Ser Asp Thr His Leu Glu
                280                 285
Glu Thr
    290
```

REFERENCES

1. Hansen M, Met O, Svane I M, Andersen M H. Cellular based cancer vaccines: type 1 polarization of dendritic cells. *Curr Med Chem* 2012; 19:4239-4246.
2. Tamura H, Dong H, Zhu G, Sica G L, Flies D B, Tamada K et al. B7-H1 co-stimulation preferentially enhances CD28-independent T-helper cell function. *Blood* 2001; 97:1809-1816.
3. Tewalt E F, Cohen J N, Rouhani S J, Guidi C J, Qiao H, Fahl S P et al. Lymphatic endothelial cells induce tolerance via PD-L1 and lack of co-stimulation leading to high-level PD-1 expression on CD8 T cells. *Blood* 2012; 120:4772-4782.
4. Seo S K, Seo D I, Park W S, Jung W K, Lee D S, Park S G et al. Attenuation of IFN-gamma-induced B7-H1 expression by 15-deoxy-delta(12,14)-prostaglandin J2 via downregulation of the Jak/STAT/IRF-1 signaling pathway. *Life Sci* 2014; 112:82-89.
5. Dong H, Zhu G, Tamada K, Chen L. B7-H1, a third member of the B7 family, co-stimulates T-cell proliferation and interleukin-10 secretion. *Nat Med* 1999; 5:1365-1369.
6. Pardoll D M. The blockade of immune checkpoints in cancer immunotherapy. *Nat Rev Cancer* 2012; 12:252-264.
7. Andersen M H. The targeting of immunosuppressive mechanisms in hematological malignancies. *Leukemia* 2014; 28:1784-1792.
8. Kozako T, Yoshimitsu M, Fujiwara H, Masamoto I, Horai S, White Y et al. PD-1/PD-L1 expression in human T-cell leukemia virus type 1 carriers and adult T-cell leukemia/lymphoma patients. *Leukemia* 2009; 23:375-382.
9. Thompson R H, Gillett M D, Cheville J C, Lohse C M, Dong H, Webster W S et al. Co-stimulatory B7-H1 in renal cell carcinoma patients: Indicator of tumor aggressiveness and potential therapeutic target. *Proc Natl Acad Sci USA* 2004; 101:17174-17179.
10. Hamanishi J, Mandai M, Iwasaki M, Okazaki T, Tanaka Y, Yamaguchi K et al. Programmed cell death 1 ligand 1 and tumor-infiltrating CD8+ T lymphocytes are prognostic factors of human ovarian cancer. *Proc Natl Acad Sci USA* 2007; 104:3360-3365.
11. Nomi T, Sho M, Akahori T, Hamada K, Kubo A, Kanehiro H et al. Clinical significance and therapeutic potential of the programmed death-1 ligand/programmed death-1 pathway in human pancreatic cancer. *Clin Cancer Res* 2007; 13:2151-2157.
12. Brahmer J R, Tykodi S S, Chow L Q, Hwu W J, Topalian S L, Hwu P et al. Safety and Activity of Anti-PD-L1 Antibody in Patients with Advanced Cancer. *N Engl J Med* 2012; 366:2455-2465.
13. Topalian S L, Hodi F S, Brahmer J R, Gettinger S N, Smith D C, McDermott D F et al. Safety, Activity, and Immune Correlates of Anti-PD-1 Antibody in Cancer. *N Engl J Med* 2012; 366:2443-2453.
14. Munir S, Andersen G H, Met O, Donia M, Frosig T M, Larsen S K et al. HLA-restricted cytotoxic T cells that are specific for the immune checkpoint ligand PD-L1 occur with high frequency in cancer patients. *Cancer Research* 2013; 73:1674-1776.
15. Munir S, Andersen G H, Woetmann A, Odum N, Becker J C, Andersen M H. Cutaneous T cell lymphoma cells are targets for immune checkpoint ligand PD-L1-specific, cytotoxic T cells. *Leukemia* 2013; 27:2251-2253.
16. Andersen M H, Sorensen R B, Brimnes M K, Svane I M, Becker J C, thor Straten P. Identification of heme oxygenase-1-specific regulatory CD8+ T cells in cancer patients. *J Clin Invest* 2009; 119:2245-2256.
17. Ahmad S M, Larsen S K, Svane I M, Andersen M H. Harnessing PD-L1-specific cytotoxic T cells for anti-leukemia immunotherapy to defeat mechanisms of immune escape mediated by the PD-1 pathway. *Leukemia* 2014; 28:236-238.
18. Munir S, Andersen G H, Svane I M, Andersen M H. The immune checkpoint regulator PD-L1 is a specific target for naturally occurring CD4+ T cells. *Oncoimmunology* 2013; 2:e23991.
19. Borch T H, Donia M, Andersen M H, Svane I M. Reorienting the immune system in the treatment of cancer by using anti-PD-1 and anti-PD-L1 antibodies. *Drug Discov Today* 2015; 20:1127-1134.
20. Andersen M H. Immune Regulation by Self-Recognition: Novel Possibilities for Anti-cancer Immunotherapy. *J Natl Cancer Inst* 2015; 107:154.
21. Yang X O, Nurieva R, Martinez G J, Kang H S, Chung Y, Pappu B P et al. Molecular antagonism and plasticity of regulatory and inflammatory T cell programs. *Immunity* 2008; 29:44-56.
22. Chen Z, O'Shea J J. Th17 cells: a new fate for differentiating helper T cells. *Immunol Res* 2008; 41:87-102.
23. Zou W, Restifo N P. T(H)17 cells in tumour immunity and immunotherapy. *Nat Rev Immunol* 2010; 10:248-256.
24. Berntsen A, Trepiakas R, Wenandy L, Geertsen P F, Thor S P, Andersen M H et al. Therapeutic dendritic cell vaccination of patients with metastatic renal cell carcinoma: a clinical phase 1/2 trial. *J Immunother* 2008; 31:771-780.
25. Rammensee H G, Falk K, Roetzschke O. MHC molecules as peptide receptors. *Curr Biol* 1995; 5:35-44.

The invention claimed is:

1. A method of treating a cancer expressing Programmed death-ligand 1 (PD-L1), the method comprising administering to an individual suffering from said cancer an effective amount of a PD-L1 peptide fragment, or a pharmaceutically acceptable salt thereof, consisting of the amino acid sequence of RTHLVILGAILLCLGVALTFIFRLRKGR (SEQ ID NO: 52), wherein the C-terminal amino acid may also comprise an amide.

2. The method of claim 1, wherein the cancer is a tumor.

3. The method of claim 1, further comprising simultaneously or sequentially administering to the individual an effective amount of an additional cancer therapy.

4. The method of claim 3, wherein the additional cancer therapy is a cytokine therapy, a T-cell therapy, an NK therapy, an immune system checkpoint inhibitor, chemotherapy, radiotherapy, immunostimulating substances, gene therapy, antibodies and/or dendritic cells.

5. The method of claim 3, wherein the additional cancer therapy is selected from the group consisting of Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

* * * * *

SEQUENCE LISTING

```
<160> NUMBER OF SEQ ID NOS: 101

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
```

```
                    85                  90                  95
Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
                130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
                210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 2
<211> LENGTH: 17
<212> TYPE: PRT
<213> ORGANISM: Homo sapiens

<400> SEQUENCE: 2

Val Ile Leu Gly Ala Ile Leu Leu Cys Leu Gly Val Ala Leu Thr Phe
1               5                   10                  15

Ile

<210> SEQ ID NO 3
<211> LENGTH: 18
<212> TYPE: PRT
<213> ORGANISM: Homo sapiens

<400> SEQUENCE: 3

Val Ile Leu Gly Ala Ile Leu Leu Cys Leu Gly Val Ala Leu Thr Phe
1               5                   10                  15

Ile Phe

<210> SEQ ID NO 4
<211> LENGTH: 19
<212> TYPE: PRT
<213> ORGANISM: Homo sapiens

<400> SEQUENCE: 4

Val Ile Leu Gly Ala Ile Leu Leu Cys Leu Gly Val Ala Leu Thr Phe
1               5                   10                  15

Ile Phe Arg
```

-continued

```
<210> SEQ ID NO 5
<211> LENGTH: 20
<212> TYPE: PRT
<213> ORGANISM: Homo sapiens

<400> SEQUENCE: 5

Val Ile Leu Gly Ala Ile Leu Leu Cys Leu Gly Val Ala Leu Thr Phe
1               5                   10                  15

Ile Phe Arg Leu
            20

<210> SEQ ID NO 6
<211> LENGTH: 21
<212> TYPE: PRT
<213> ORGANISM: Homo sapiens

<400> SEQUENCE: 6

Val Ile Leu Gly Ala Ile Leu Leu Cys Leu Gly Val Ala Leu Thr Phe
1               5                   10                  15

Ile Phe Arg Leu Arg
            20

<210> SEQ ID NO 7
<211> LENGTH: 22
<212> TYPE: PRT
<213> ORGANISM: Homo sapiens

<400> SEQUENCE: 7

Val Ile Leu Gly Ala Ile Leu Leu Cys Leu Gly Val Ala Leu Thr Phe
1               5                   10                  15

Ile Phe Arg Leu Arg Lys
            20

<210> SEQ ID NO 8
<211> LENGTH: 24
<212> TYPE: PRT
<213> ORGANISM: Homo sapiens

<400> SEQUENCE: 8

Val Ile Leu Gly Ala Ile Leu Leu Cys Leu Gly Val Ala Leu Thr Phe
1               5                   10                  15

Ile Phe Arg Leu Arg Lys Gly Arg
            20

<210> SEQ ID NO 9
<211> LENGTH: 25
<212> TYPE: PRT
<213> ORGANISM: Homo sapiens

<400> SEQUENCE: 9

Val Ile Leu Gly Ala Ile Leu Leu Cys Leu Gly Val Ala Leu Thr Phe
1               5                   10                  15

Ile Phe Arg Leu Arg Lys Gly Arg Met
            20                  25

<210> SEQ ID NO 10
<211> LENGTH: 26
<212> TYPE: PRT
<213> ORGANISM: Homo sapiens

<400> SEQUENCE: 10
```

```
Val Ile Leu Gly Ala Ile Leu Leu Cys Leu Gly Val Ala Leu Thr Phe
1               5                   10                  15

Ile Phe Arg Leu Arg Lys Gly Arg Met Met
            20                  25
```

<210> SEQ ID NO 11
<211> LENGTH: 27
<212> TYPE: PRT
<213> ORGANISM: Homo sapiens

<400> SEQUENCE: 11

```
Val Ile Leu Gly Ala Ile Leu Leu Cys Leu Gly Val Ala Leu Thr Phe
1               5                   10                  15

Ile Phe Arg Leu Arg Lys Gly Arg Met Met Asp
            20                  25
```

<210> SEQ ID NO 12
<211> LENGTH: 18
<212> TYPE: PRT
<213> ORGANISM: Homo sapiens

<400> SEQUENCE: 12

```
Leu Val Ile Leu Gly Ala Ile Leu Leu Cys Leu Gly Val Ala Leu Thr
1               5                   10                  15

Phe Ile
```

<210> SEQ ID NO 13
<211> LENGTH: 19
<212> TYPE: PRT
<213> ORGANISM: Homo sapiens

<400> SEQUENCE: 13

```
Leu Val Ile Leu Gly Ala Ile Leu Leu Cys Leu Gly Val Ala Leu Thr
1               5                   10                  15

Phe Ile Phe
```

<210> SEQ ID NO 14
<211> LENGTH: 20
<212> TYPE: PRT
<213> ORGANISM: Homo sapiens

<400> SEQUENCE: 14

```
Leu Val Ile Leu Gly Ala Ile Leu Leu Cys Leu Gly Val Ala Leu Thr
1               5                   10                  15

Phe Ile Phe Arg
            20
```

<210> SEQ ID NO 15
<211> LENGTH: 21
<212> TYPE: PRT
<213> ORGANISM: Homo sapiens

<400> SEQUENCE: 15

```
Leu Val Ile Leu Gly Ala Ile Leu Leu Cys Leu Gly Val Ala Leu Thr
1               5                   10                  15

Phe Ile Phe Arg Leu
            20
```

<210> SEQ ID NO 16
<211> LENGTH: 22
<212> TYPE: PRT
<213> ORGANISM: Homo sapiens

```
<400> SEQUENCE: 16

Leu Val Ile Leu Gly Ala Ile Leu Leu Cys Leu Gly Val Ala Leu Thr
1               5                   10                  15

Phe Ile Phe Arg Leu Arg
            20

<210> SEQ ID NO 17
<211> LENGTH: 23
<212> TYPE: PRT
<213> ORGANISM: Homo sapiens

<400> SEQUENCE: 17

Leu Val Ile Leu Gly Ala Ile Leu Leu Cys Leu Gly Val Ala Leu Thr
1               5                   10                  15

Phe Ile Phe Arg Leu Arg Lys
            20

<210> SEQ ID NO 18
<211> LENGTH: 24
<212> TYPE: PRT
<213> ORGANISM: Homo sapiens

<400> SEQUENCE: 18

Leu Val Ile Leu Gly Ala Ile Leu Leu Cys Leu Gly Val Ala Leu Thr
1               5                   10                  15

Phe Ile Phe Arg Leu Arg Lys Gly
            20

<210> SEQ ID NO 19
<211> LENGTH: 25
<212> TYPE: PRT
<213> ORGANISM: Homo sapiens

<400> SEQUENCE: 19

Leu Val Ile Leu Gly Ala Ile Leu Leu Cys Leu Gly Val Ala Leu Thr
1               5                   10                  15

Phe Ile Phe Arg Leu Arg Lys Gly Arg
            20                  25

<210> SEQ ID NO 20
<211> LENGTH: 26
<212> TYPE: PRT
<213> ORGANISM: Homo sapiens

<400> SEQUENCE: 20

Leu Val Ile Leu Gly Ala Ile Leu Leu Cys Leu Gly Val Ala Leu Thr
1               5                   10                  15

Phe Ile Phe Arg Leu Arg Lys Gly Arg Met
            20                  25

<210> SEQ ID NO 21
<211> LENGTH: 27
<212> TYPE: PRT
<213> ORGANISM: Homo sapiens

<400> SEQUENCE: 21

Leu Val Ile Leu Gly Ala Ile Leu Leu Cys Leu Gly Val Ala Leu Thr
1               5                   10                  15

Phe Ile Phe Arg Leu Arg Lys Gly Arg Met Met
            20                  25
```

<210> SEQ ID NO 22
<211> LENGTH: 28
<212> TYPE: PRT
<213> ORGANISM: Homo sapiens

<400> SEQUENCE: 22

Leu Val Ile Leu Gly Ala Ile Leu Leu Cys Leu Gly Val Ala Leu Thr
1               5                   10                  15

Phe Ile Phe Arg Leu Arg Lys Gly Arg Met Met Asp
            20                  25

<210> SEQ ID NO 23
<211> LENGTH: 19
<212> TYPE: PRT
<213> ORGANISM: Homo sapiens

<400> SEQUENCE: 23

His Leu Val Ile Leu Gly Ala Ile Leu Leu Cys Leu Gly Val Ala Leu
1               5                   10                  15

Thr Phe Ile

<210> SEQ ID NO 24
<211> LENGTH: 20
<212> TYPE: PRT
<213> ORGANISM: Homo sapiens

<400> SEQUENCE: 24

His Leu Val Ile Leu Gly Ala Ile Leu Leu Cys Leu Gly Val Ala Leu
1               5                   10                  15

Thr Phe Ile Phe
            20

<210> SEQ ID NO 25
<211> LENGTH: 21
<212> TYPE: PRT
<213> ORGANISM: Homo sapiens

<400> SEQUENCE: 25

His Leu Val Ile Leu Gly Ala Ile Leu Leu Cys Leu Gly Val Ala Leu
1               5                   10                  15

Thr Phe Ile Phe Arg
            20

<210> SEQ ID NO 26
<211> LENGTH: 22
<212> TYPE: PRT
<213> ORGANISM: Homo sapiens

<400> SEQUENCE: 26

His Leu Val Ile Leu Gly Ala Ile Leu Leu Cys Leu Gly Val Ala Leu
1               5                   10                  15

Thr Phe Ile Phe Arg Leu
            20

<210> SEQ ID NO 27
<211> LENGTH: 23
<212> TYPE: PRT
<213> ORGANISM: Homo sapiens

<400> SEQUENCE: 27

His Leu Val Ile Leu Gly Ala Ile Leu Leu Cys Leu Gly Val Ala Leu
1               5                   10                  15

Thr Phe Ile Phe Arg Leu Arg
            20

<210> SEQ ID NO 28
<211> LENGTH: 24
<212> TYPE: PRT
<213> ORGANISM: Homo sapiens

<400> SEQUENCE: 28

His Leu Val Ile Leu Gly Ala Ile Leu Leu Cys Leu Gly Val Ala Leu
1               5                   10                  15

Thr Phe Ile Phe Arg Leu Arg Lys
            20

<210> SEQ ID NO 29
<211> LENGTH: 25
<212> TYPE: PRT
<213> ORGANISM: Homo sapiens

<400> SEQUENCE: 29

His Leu Val Ile Leu Gly Ala Ile Leu Leu Cys Leu Gly Val Ala Leu
1               5                   10                  15

Thr Phe Ile Phe Arg Leu Arg Lys Gly
            20                  25

<210> SEQ ID NO 30
<211> LENGTH: 26
<212> TYPE: PRT
<213> ORGANISM: Homo sapiens

<400> SEQUENCE: 30

His Leu Val Ile Leu Gly Ala Ile Leu Leu Cys Leu Gly Val Ala Leu
1               5                   10                  15

Thr Phe Ile Phe Arg Leu Arg Lys Gly Arg
            20                  25

<210> SEQ ID NO 31
<211> LENGTH: 27
<212> TYPE: PRT
<213> ORGANISM: Homo sapiens

<400> SEQUENCE: 31

His Leu Val Ile Leu Gly Ala Ile Leu Leu Cys Leu Gly Val Ala Leu
1               5                   10                  15

Thr Phe Ile Phe Arg Leu Arg Lys Gly Arg Met
            20                  25

<210> SEQ ID NO 32
<211> LENGTH: 28
<212> TYPE: PRT
<213> ORGANISM: Homo sapiens

<400> SEQUENCE: 32

His Leu Val Ile Leu Gly Ala Ile Leu Leu Cys Leu Gly Val Ala Leu
1               5                   10                  15

Thr Phe Ile Phe Arg Leu Arg Lys Gly Arg Met Met
            20                  25

<210> SEQ ID NO 33
<211> LENGTH: 29
<212> TYPE: PRT
<213> ORGANISM: Homo sapiens -continued

```
<400> SEQUENCE: 33

His Leu Val Ile Leu Gly Ala Ile Leu Leu Cys Leu Gly Val Ala Leu
1               5                   10                  15

Thr Phe Ile Phe Arg Leu Arg Lys Gly Arg Met Met Asp
            20                  25

<210> SEQ ID NO 34
<211> LENGTH: 20
<212> TYPE: PRT
<213> ORGANISM: Homo sapiens

<400> SEQUENCE: 34

Thr His Leu Val Ile Leu Gly Ala Ile Leu Leu Cys Leu Gly Val Ala
1               5                   10                  15

Leu Thr Phe Ile
            20

<210> SEQ ID NO 35
<211> LENGTH: 21
<212> TYPE: PRT
<213> ORGANISM: Homo sapiens

<400> SEQUENCE: 35

Thr His Leu Val Ile Leu Gly Ala Ile Leu Leu Cys Leu Gly Val Ala
1               5                   10                  15

Leu Thr Phe Ile Phe
            20

<210> SEQ ID NO 36
<211> LENGTH: 22
<212> TYPE: PRT
<213> ORGANISM: Homo sapiens

<400> SEQUENCE: 36

Thr His Leu Val Ile Leu Gly Ala Ile Leu Leu Cys Leu Gly Val Ala
1               5                   10                  15

Leu Thr Phe Ile Phe Arg
            20

<210> SEQ ID NO 37
<211> LENGTH: 23
<212> TYPE: PRT
<213> ORGANISM: Homo sapiens

<400> SEQUENCE: 37

Thr His Leu Val Ile Leu Gly Ala Ile Leu Leu Cys Leu Gly Val Ala
1               5                   10                  15

Leu Thr Phe Ile Phe Arg Leu
            20

<210> SEQ ID NO 38
<211> LENGTH: 24
<212> TYPE: PRT
<213> ORGANISM: Homo sapiens

<400> SEQUENCE: 38

Thr His Leu Val Ile Leu Gly Ala Ile Leu Leu Cys Leu Gly Val Ala
1               5                   10                  15

Leu Thr Phe Ile Phe Arg Leu Arg
            20
```

-continued

<210> SEQ ID NO 39
<211> LENGTH: 25
<212> TYPE: PRT
<213> ORGANISM: Homo sapiens

<400> SEQUENCE: 39

Thr His Leu Val Ile Leu Gly Ala Ile Leu Leu Cys Leu Gly Val Ala
1               5                   10                  15

Leu Thr Phe Ile Phe Arg Leu Arg Lys
            20                  25

<210> SEQ ID NO 40
<211> LENGTH: 26
<212> TYPE: PRT
<213> ORGANISM: Homo sapiens

<400> SEQUENCE: 40

Thr His Leu Val Ile Leu Gly Ala Ile Leu Leu Cys Leu Gly Val Ala
1               5                   10                  15

Leu Thr Phe Ile Phe Arg Leu Arg Lys Gly
            20                  25

<210> SEQ ID NO 41
<211> LENGTH: 27
<212> TYPE: PRT
<213> ORGANISM: Homo sapiens

<400> SEQUENCE: 41

Thr His Leu Val Ile Leu Gly Ala Ile Leu Leu Cys Leu Gly Val Ala
1               5                   10                  15

Leu Thr Phe Ile Phe Arg Leu Arg Lys Gly Arg
            20                  25

<210> SEQ ID NO 42
<211> LENGTH: 28
<212> TYPE: PRT
<213> ORGANISM: Homo sapiens

<400> SEQUENCE: 42

Thr His Leu Val Ile Leu Gly Ala Ile Leu Leu Cys Leu Gly Val Ala
1               5                   10                  15

Leu Thr Phe Ile Phe Arg Leu Arg Lys Gly Arg Met
            20                  25

<210> SEQ ID NO 43
<211> LENGTH: 29
<212> TYPE: PRT
<213> ORGANISM: Homo sapiens

<400> SEQUENCE: 43

Thr His Leu Val Ile Leu Gly Ala Ile Leu Leu Cys Leu Gly Val Ala
1               5                   10                  15

Leu Thr Phe Ile Phe Arg Leu Arg Lys Gly Arg Met Met
            20                  25

<210> SEQ ID NO 44
<211> LENGTH: 30
<212> TYPE: PRT
<213> ORGANISM: Homo sapiens

<400> SEQUENCE: 44

Thr His Leu Val Ile Leu Gly Ala Ile Leu Leu Cys Leu Gly Val Ala

```
1               5                  10                 15
Leu Thr Phe Ile Phe Arg Leu Arg Lys Gly Arg Met Met Asp
        20                  25                 30
```

<210> SEQ ID NO 45
<211> LENGTH: 21
<212> TYPE: PRT
<213> ORGANISM: Homo sapiens

<400> SEQUENCE: 45

```
Arg Thr His Leu Val Ile Leu Gly Ala Ile Leu Leu Cys Leu Gly Val
1               5                  10                 15
Ala Leu Thr Phe Ile
        20
```

<210> SEQ ID NO 46
<211> LENGTH: 22
<212> TYPE: PRT
<213> ORGANISM: Homo sapiens

<400> SEQUENCE: 46

```
Arg Thr His Leu Val Ile Leu Gly Ala Ile Leu Leu Cys Leu Gly Val
1               5                  10                 15
Ala Leu Thr Phe Ile Phe
        20
```

<210> SEQ ID NO 47
<211> LENGTH: 23
<212> TYPE: PRT
<213> ORGANISM: Homo sapiens

<400> SEQUENCE: 47

```
Arg Thr His Leu Val Ile Leu Gly Ala Ile Leu Leu Cys Leu Gly Val
1               5                  10                 15
Ala Leu Thr Phe Ile Phe Arg
        20
```

<210> SEQ ID NO 48
<211> LENGTH: 24
<212> TYPE: PRT
<213> ORGANISM: Homo sapiens

<400> SEQUENCE: 48

```
Arg Thr His Leu Val Ile Leu Gly Ala Ile Leu Leu Cys Leu Gly Val
1               5                  10                 15
Ala Leu Thr Phe Ile Phe Arg Leu
        20
```

<210> SEQ ID NO 49
<211> LENGTH: 25
<212> TYPE: PRT
<213> ORGANISM: Homo sapiens

<400> SEQUENCE: 49

```
Arg Thr His Leu Val Ile Leu Gly Ala Ile Leu Leu Cys Leu Gly Val
1               5                  10                 15
Ala Leu Thr Phe Ile Phe Arg Leu Arg
        20                  25
```

<210> SEQ ID NO 50
<211> LENGTH: 26
<212> TYPE: PRT

-continued

<213> ORGANISM: Homo sapiens

<400> SEQUENCE: 50

Arg Thr His Leu Val Ile Leu Gly Ala Ile Leu Leu Cys Leu Gly Val
1               5                   10                  15

Ala Leu Thr Phe Ile Phe Arg Leu Arg Lys
            20                  25

<210> SEQ ID NO 51
<211> LENGTH: 27
<212> TYPE: PRT
<213> ORGANISM: Homo sapiens

<400> SEQUENCE: 51

Arg Thr His Leu Val Ile Leu Gly Ala Ile Leu Leu Cys Leu Gly Val
1               5                   10                  15

Ala Leu Thr Phe Ile Phe Arg Leu Arg Lys Gly
            20                  25

<210> SEQ ID NO 52
<211> LENGTH: 28
<212> TYPE: PRT
<213> ORGANISM: Homo sapiens

<400> SEQUENCE: 52

Arg Thr His Leu Val Ile Leu Gly Ala Ile Leu Leu Cys Leu Gly Val
1               5                   10                  15

Ala Leu Thr Phe Ile Phe Arg Leu Arg Lys Gly Arg
            20                  25

<210> SEQ ID NO 53
<211> LENGTH: 29
<212> TYPE: PRT
<213> ORGANISM: Homo sapiens

<400> SEQUENCE: 53

Arg Thr His Leu Val Ile Leu Gly Ala Ile Leu Leu Cys Leu Gly Val
1               5                   10                  15

Ala Leu Thr Phe Ile Phe Arg Leu Arg Lys Gly Arg Met
            20                  25

<210> SEQ ID NO 54
<211> LENGTH: 30
<212> TYPE: PRT
<213> ORGANISM: Homo sapiens

<400> SEQUENCE: 54

Arg Thr His Leu Val Ile Leu Gly Ala Ile Leu Leu Cys Leu Gly Val
1               5                   10                  15

Ala Leu Thr Phe Ile Phe Arg Leu Arg Lys Gly Arg Met Met
            20                  25                  30

<210> SEQ ID NO 55
<211> LENGTH: 31
<212> TYPE: PRT
<213> ORGANISM: Homo sapiens

<400> SEQUENCE: 55

Arg Thr His Leu Val Ile Leu Gly Ala Ile Leu Leu Cys Leu Gly Val
1               5                   10                  15

Ala Leu Thr Phe Ile Phe Arg Leu Arg Lys Gly Arg Met Met Asp
            20                  25                  30

<210> SEQ ID NO 56
<211> LENGTH: 22
<212> TYPE: PRT
<213> ORGANISM: Homo sapiens

<400> SEQUENCE: 56

Glu Arg Thr His Leu Val Ile Leu Gly Ala Ile Leu Leu Cys Leu Gly
1               5                   10                  15

Val Ala Leu Thr Phe Ile
            20

<210> SEQ ID NO 57
<211> LENGTH: 23
<212> TYPE: PRT
<213> ORGANISM: Homo sapiens

<400> SEQUENCE: 57

Glu Arg Thr His Leu Val Ile Leu Gly Ala Ile Leu Leu Cys Leu Gly
1               5                   10                  15

Val Ala Leu Thr Phe Ile Phe
            20

<210> SEQ ID NO 58
<211> LENGTH: 24
<212> TYPE: PRT
<213> ORGANISM: Homo sapiens

<400> SEQUENCE: 58

Glu Arg Thr His Leu Val Ile Leu Gly Ala Ile Leu Leu Cys Leu Gly
1               5                   10                  15

Val Ala Leu Thr Phe Ile Phe Arg
            20

<210> SEQ ID NO 59
<211> LENGTH: 25
<212> TYPE: PRT
<213> ORGANISM: Homo sapiens

<400> SEQUENCE: 59

Glu Arg Thr His Leu Val Ile Leu Gly Ala Ile Leu Leu Cys Leu Gly
1               5                   10                  15

Val Ala Leu Thr Phe Ile Phe Arg Leu
            20                  25

<210> SEQ ID NO 60
<211> LENGTH: 26
<212> TYPE: PRT
<213> ORGANISM: Homo sapiens

<400> SEQUENCE: 60

Glu Arg Thr His Leu Val Ile Leu Gly Ala Ile Leu Leu Cys Leu Gly
1               5                   10                  15

Val Ala Leu Thr Phe Ile Phe Arg Leu Arg
            20                  25

<210> SEQ ID NO 61
<211> LENGTH: 27
<212> TYPE: PRT
<213> ORGANISM: Homo sapiens

<400> SEQUENCE: 61

Glu Arg Thr His Leu Val Ile Leu Gly Ala Ile Leu Leu Cys Leu Gly
1               5                   10                  15

Val Ala Leu Thr Phe Ile Phe Arg Leu Arg Lys
            20                  25

<210> SEQ ID NO 62
<211> LENGTH: 28
<212> TYPE: PRT
<213> ORGANISM: Homo sapiens

<400> SEQUENCE: 62

Glu Arg Thr His Leu Val Ile Leu Gly Ala Ile Leu Leu Cys Leu Gly
1               5                   10                  15

Val Ala Leu Thr Phe Ile Phe Arg Leu Arg Lys Gly
            20                  25

<210> SEQ ID NO 63
<211> LENGTH: 29
<212> TYPE: PRT
<213> ORGANISM: Homo sapiens

<400> SEQUENCE: 63

Glu Arg Thr His Leu Val Ile Leu Gly Ala Ile Leu Leu Cys Leu Gly
1               5                   10                  15

Val Ala Leu Thr Phe Ile Phe Arg Leu Arg Lys Gly Arg
            20                  25

<210> SEQ ID NO 64
<211> LENGTH: 30
<212> TYPE: PRT
<213> ORGANISM: Homo sapiens

<400> SEQUENCE: 64

Glu Arg Thr His Leu Val Ile Leu Gly Ala Ile Leu Leu Cys Leu Gly
1               5                   10                  15

Val Ala Leu Thr Phe Ile Phe Arg Leu Arg Lys Gly Arg Met
            20                  25                  30

<210> SEQ ID NO 65
<211> LENGTH: 31
<212> TYPE: PRT
<213> ORGANISM: Homo sapiens

<400> SEQUENCE: 65

Glu Arg Thr His Leu Val Ile Leu Gly Ala Ile Leu Leu Cys Leu Gly
1               5                   10                  15

Val Ala Leu Thr Phe Ile Phe Arg Leu Arg Lys Gly Arg Met Met
            20                  25                  30

<210> SEQ ID NO 66
<211> LENGTH: 32
<212> TYPE: PRT
<213> ORGANISM: Homo sapiens

<400> SEQUENCE: 66

Glu Arg Thr His Leu Val Ile Leu Gly Ala Ile Leu Leu Cys Leu Gly
1               5                   10                  15

Val Ala Leu Thr Phe Ile Phe Arg Leu Arg Lys Gly Arg Met Met Asp
            20                  25                  30

<210> SEQ ID NO 67
<211> LENGTH: 23

```
<212> TYPE: PRT
<213> ORGANISM: Homo sapiens

<400> SEQUENCE: 67

Asn Glu Arg Thr His Leu Val Ile Leu Gly Ala Ile Leu Leu Cys Leu
1               5                   10                  15

Gly Val Ala Leu Thr Phe Ile
            20

<210> SEQ ID NO 68
<211> LENGTH: 24
<212> TYPE: PRT
<213> ORGANISM: Homo sapiens

<400> SEQUENCE: 68

Asn Glu Arg Thr His Leu Val Ile Leu Gly Ala Ile Leu Leu Cys Leu
1               5                   10                  15

Gly Val Ala Leu Thr Phe Ile Phe
            20

<210> SEQ ID NO 69
<211> LENGTH: 25
<212> TYPE: PRT
<213> ORGANISM: Homo sapiens

<400> SEQUENCE: 69

Asn Glu Arg Thr His Leu Val Ile Leu Gly Ala Ile Leu Leu Cys Leu
1               5                   10                  15

Gly Val Ala Leu Thr Phe Ile Phe Arg
            20                  25

<210> SEQ ID NO 70
<211> LENGTH: 26
<212> TYPE: PRT
<213> ORGANISM: Homo sapiens

<400> SEQUENCE: 70

Asn Glu Arg Thr His Leu Val Ile Leu Gly Ala Ile Leu Leu Cys Leu
1               5                   10                  15

Gly Val Ala Leu Thr Phe Ile Phe Arg Leu
            20                  25

<210> SEQ ID NO 71
<211> LENGTH: 27
<212> TYPE: PRT
<213> ORGANISM: Homo sapiens

<400> SEQUENCE: 71

Asn Glu Arg Thr His Leu Val Ile Leu Gly Ala Ile Leu Leu Cys Leu
1               5                   10                  15

Gly Val Ala Leu Thr Phe Ile Phe Arg Leu Arg
            20                  25

<210> SEQ ID NO 72
<211> LENGTH: 28
<212> TYPE: PRT
<213> ORGANISM: Homo sapiens

<400> SEQUENCE: 72

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys
```

-continued

```
                20                  25

<210> SEQ ID NO 73
<211> LENGTH: 29
<212> TYPE: PRT
<213> ORGANISM: Homo sapiens

<400> SEQUENCE: 73

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys Gly
            20                  25

<210> SEQ ID NO 74
<211> LENGTH: 30
<212> TYPE: PRT
<213> ORGANISM: Homo sapiens

<400> SEQUENCE: 74

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys Gly Arg
            20                  25                  30

<210> SEQ ID NO 75
<211> LENGTH: 31
<212> TYPE: PRT
<213> ORGANISM: Homo sapiens

<400> SEQUENCE: 75

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys Gly Arg Met
            20                  25                  30

<210> SEQ ID NO 76
<211> LENGTH: 32
<212> TYPE: PRT
<213> ORGANISM: Homo sapiens

<400> SEQUENCE: 76

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys Gly Arg Met Met
            20                  25                  30

<210> SEQ ID NO 77
<211> LENGTH: 33
<212> TYPE: PRT
<213> ORGANISM: Homo sapiens

<400> SEQUENCE: 77

Asn Glu Arg Thr His Leu Val Ile Leu Gly Ala Ile Leu Leu Cys Leu
1               5                   10                  15

Gly Val Ala Leu Thr Phe Ile Phe Arg Leu Arg Lys Gly Arg Met Met
            20                  25                  30

Asp

<210> SEQ ID NO 78
<211> LENGTH: 19
<212> TYPE: PRT
<213> ORGANISM: Artificial Sequence
```

```
<220> FEATURE:
<223> OTHER INFORMATION: General formula corresponding to the peptides
      of the invention
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (19)..(19)
<223> OTHER INFORMATION: Xaa is any amino acid

<400> SEQUENCE: 78

Xaa Val Ile Leu Gly Ala Ile Leu Leu Cys Leu Gly Val Ala Leu Thr
1               5                   10                  15

Phe Ile Xaa

<210> SEQ ID NO 79
<211> LENGTH: 4
<212> TYPE: PRT
<213> ORGANISM: Artificial Sequence
<220> FEATURE:
<223> OTHER INFORMATION: N-terminal amino acid sequences which may be
      added to formula of SEQ ID NO:78

<400> SEQUENCE: 79

Arg Thr His Leu
1

<210> SEQ ID NO 80
<211> LENGTH: 5
<212> TYPE: PRT
<213> ORGANISM: Artificial Sequence
<220> FEATURE:
<223> OTHER INFORMATION: N-terminal amino acid sequences which may be
      added to formula of SEQ ID NO:78

<400> SEQUENCE: 80

Glu Arg Thr His Leu
1               5

<210> SEQ ID NO 81
<211> LENGTH: 6
<212> TYPE: PRT
<213> ORGANISM: Artificial Sequence
<220> FEATURE:
<223> OTHER INFORMATION: N-terminal amino acid sequences which may be
      added to formula of SEQ ID NO:78

<400> SEQUENCE: 81

Asn Glu Arg Thr His Leu
1               5

<210> SEQ ID NO 82
<211> LENGTH: 4
<212> TYPE: PRT
<213> ORGANISM: Artificial Sequence
<220> FEATURE:
<223> OTHER INFORMATION: C terminal amino acid sequences which may be
      added to the formula of SEQ ID NO: 78.

<400> SEQUENCE: 82

Phe Arg Leu Arg
1

<210> SEQ ID NO 83
<211> LENGTH: 5
<212> TYPE: PRT
```

```
<213> ORGANISM: Artificial Sequence
<220> FEATURE:
<223> OTHER INFORMATION: C terminal amino acid sequences which may be
      added to the formula of SEQ ID NO: 78.

<400> SEQUENCE: 83

Phe Arg Leu Arg Lys
1               5

<210> SEQ ID NO 84
<211> LENGTH: 6
<212> TYPE: PRT
<213> ORGANISM: Artificial Sequence
<220> FEATURE:
<223> OTHER INFORMATION: C terminal amino acid sequences which may be
      added to the formula of SEQ ID NO: 78

<400> SEQUENCE: 84

Phe Arg Leu Arg Lys Gly
1               5

<210> SEQ ID NO 85
<211> LENGTH: 7
<212> TYPE: PRT
<213> ORGANISM: Artificial Sequence
<220> FEATURE:
<223> OTHER INFORMATION: C terminal amino acid sequences which may be
      added to the formula of SEQ ID NO: 78

<400> SEQUENCE: 85

Phe Arg Leu Arg Lys Gly Arg
1               5

<210> SEQ ID NO 86
<211> LENGTH: 8
<212> TYPE: PRT
<213> ORGANISM: Artificial Sequence
<220> FEATURE:
<223> OTHER INFORMATION: C terminal amino acid sequences which may be
      added to the formula of SEQ ID NO: 78

<400> SEQUENCE: 86

Phe Arg Leu Arg Lys Gly Arg Met
1               5

<210> SEQ ID NO 87
<211> LENGTH: 9
<212> TYPE: PRT
<213> ORGANISM: Artificial Sequence
<220> FEATURE:
<223> OTHER INFORMATION: C terminal amino acid sequences which may be
      added to the formula of SEQ ID NO: 78

<400> SEQUENCE: 87

Phe Arg Leu Arg Lys Gly Arg Met Met
1               5

<210> SEQ ID NO 88
<211> LENGTH: 10
<212> TYPE: PRT
<213> ORGANISM: Artificial Sequence
<220> FEATURE:
<223> OTHER INFORMATION: C terminal amino acid sequences which may be
      added to the formula of SEQ ID NO: 78

<400> SEQUENCE: 88

Phe Arg Leu Arg Lys Gly Arg Met Met Asp
1               5                   10
```

<210> SEQ ID NO 89
<211> LENGTH: 19
<212> TYPE: PRT
<213> ORGANISM: Homo sapiens

<400> SEQUENCE: 89

Phe Met Thr Tyr Trp His Leu Leu Asn Ala Phe Thr Val Thr Val Pro
1               5                   10                  15

Lys Asp Leu

<210> SEQ ID NO 90
<211> LENGTH: 9
<212> TYPE: PRT
<213> ORGANISM: Homo sapiens

<400> SEQUENCE: 90

Leu Leu Asn Ala Phe Thr Val Thr Val
1               5

<210> SEQ ID NO 91
<211> LENGTH: 23
<212> TYPE: PRT
<213> ORGANISM: Homo sapiens

<400> SEQUENCE: 91

Val Ile Leu Gly Ala Ile Leu Cys Leu Gly Val Ala Leu Thr Phe
1               5                   10                  15

Ile Phe Arg Leu Arg Lys Gly
            20

<210> SEQ ID NO 92
<211> LENGTH: 9
<212> TYPE: PRT
<213> ORGANISM: Homo sapiens

<400> SEQUENCE: 92

Cys Leu Gly Val Ala Leu Thr Phe Ile
1               5

<210> SEQ ID NO 93
<211> LENGTH: 20
<212> TYPE: PRT
<213> ORGANISM: Artificial Sequence
<220> FEATURE:
<223> OTHER INFORMATION: Control peptide used in the Examples

<400> SEQUENCE: 93

Gly Ala Arg Val Glu Arg Val Asp Phe Gly Asn Phe Val Phe Asn Ile
1               5                   10                  15

Ser Val Leu Trp
            20

<210> SEQ ID NO 94
<211> LENGTH: 9
<212> TYPE: PRT
<213> ORGANISM: Artificial Sequence
<220> FEATURE:
<223> OTHER INFORMATION: Control peptide used in Examples

<400> SEQUENCE: 94

Ile Leu Lys Glu Pro Val His Gly Val
1               5

<210> SEQ ID NO 95
<211> LENGTH: 290
<212> TYPE: PRT
<213> ORGANISM: Mus musculus

<400> SEQUENCE: 95

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 96
<211> LENGTH: 18
<212> TYPE: PRT
<213> ORGANISM: Mus musculus

<400> SEQUENCE: 96

Met Arg Ile Phe Ala Gly Ile Ile Phe Thr Ala Cys Cys His Leu Leu
1               5                   10                  15

Arg Ala

```
<210> SEQ ID NO 97
<211> LENGTH: 19
<212> TYPE: PRT
<213> ORGANISM: Mus musculus

<400> SEQUENCE: 97

Phe Thr Ala Cys Cys His Leu Leu Arg Ala Phe Thr Ile Thr Ala Pro
1               5                   10                  15

Lys Asp Leu

<210> SEQ ID NO 98
<211> LENGTH: 25
<212> TYPE: PRT
<213> ORGANISM: Mus musculus

<400> SEQUENCE: 98

Trp Val Leu Leu Gly Ser Ile Leu Leu Phe Leu Ile Val Val Ser Thr
1               5                   10                  15

Val Leu Leu Phe Leu Arg Lys Gln Val
            20                  25

<210> SEQ ID NO 99
<211> LENGTH: 20
<212> TYPE: PRT
<213> ORGANISM: Mus musculus

<400> SEQUENCE: 99

Thr Val Leu Leu Phe Leu Arg Lys Gln Val Arg Met Leu Asp Val Glu
1               5                   10                  15

Lys Cys Gly Val
            20

<210> SEQ ID NO 100
<211> LENGTH: 25
<212> TYPE: PRT
<213> ORGANISM: Mus musculus

<400> SEQUENCE: 100

Met Leu Asp Val Glu Lys Cys Gly Val Glu Asp Thr Ser Ser Lys Asn
1               5                   10                  15

Arg Asn Asp Thr Gln Phe Glu Glu Thr
            20                  25

<210> SEQ ID NO 101
<211> LENGTH: 10
<212> TYPE: PRT
<213> ORGANISM: Mus musculus

<400> SEQUENCE: 101

Gly Ile Ile Phe Thr Ala Cys Cys His Leu
1               5                   10
```